United States Patent
Kathirgamanathan et al.

(10) Patent No.: US 9,221,770 B2
(45) Date of Patent: Dec. 29, 2015

(54) COMPOUNDS HAVING ELECTRON TRANSPORT PROPERTIES, THEIR PREPARATION AND USE

(75) Inventors: Poopathy Kathirgamanathan, North Harrow (GB); Sivagnanasundram Surendrakumar, Middlesex (GB); Yun Fu Chan, Cleveland (GB)

(73) Assignee: Merck Patent GmbH, Darmstadt (DE)

( * ) Notice: Subject to any disclaimer, the term of this patent is extended or adjusted under 35 U.S.C. 154(b) by 764 days.

(21) Appl. No.: 13/001,292

(22) PCT Filed: Aug. 6, 2009

(86) PCT No.: PCT/EP2009/005708
§ 371 (c)(1),
(2), (4) Date: Dec. 23, 2010

(87) PCT Pub. No.: WO2010/020352
PCT Pub. Date: Feb. 25, 2010

(65) Prior Publication Data
US 2011/0108819 A1    May 12, 2011

(30) Foreign Application Priority Data
Aug. 18, 2008    (GB) .................................. 0814954.4

(51) Int. Cl.
*H01L 51/54* (2006.01)
*C07D 263/57* (2006.01)
*C07F 5/00* (2006.01)
(Continued)

(52) U.S. Cl.
CPC ............ *C07D 263/57* (2013.01); *C07D 277/64* (2013.01); *C07F 1/005* (2013.01); *C07F 5/003* (2013.01); *C07F 5/02* (2013.01); *C07F 7/025* (2013.01); *C07F 9/005* (2013.01);
(Continued)

(58) Field of Classification Search
CPC ........ H01L 51/0079–51/0081; H01L 51/0091; H01L 51/0092; H01L 51/5072; C07F 1/005; C07F 3/003; C07F 5/02; C07F 5/069; C07F 7/025; C07F 7/006
See application file for complete search history.

(56) References Cited

U.S. PATENT DOCUMENTS 5,747,183 A    5/1998  Shi et al.
5,922,480 A *  7/1999  Nakamura et al. ............ 428/690
(Continued)

FOREIGN PATENT DOCUMENTS

EP          652273 A1    5/1995
JP      06-336586 A    12/1994
(Continued)

OTHER PUBLICATIONS

English language machine translation of JP 2000-030864 A, 2000.*
(Continued)

*Primary Examiner* — Michael H Wilson
(74) *Attorney, Agent, or Firm* — Drinker Biddle & Reath LLP

(57) ABSTRACT

The invention provides new compounds of the formula I, II or III. These compounds can be used as electron transport materials in optical light emitting diodes (OLEDs). The compounds of the formula I, II and III are as follows:

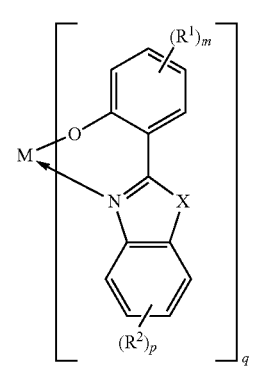

I

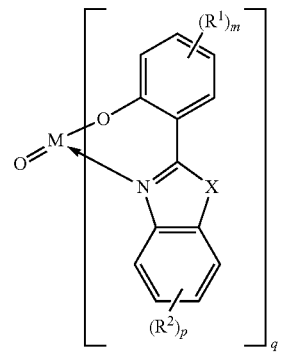

II

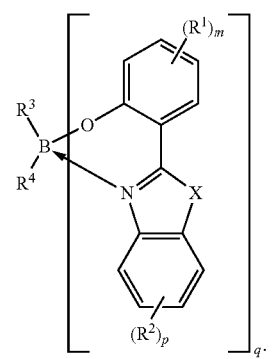

III

16 Claims, 2 Drawing Sheets

(51) Int. Cl.

| | |
|---|---|
| *C07F 1/00* | (2006.01) |
| *H01L 51/00* | (2006.01) |
| *H01L 51/50* | (2006.01) |
| *C07D 277/64* | (2006.01) |
| *C07F 5/02* | (2006.01) |
| *C07F 7/02* | (2006.01) |
| *C07F 9/00* | (2006.01) |

(52) U.S. Cl.
CPC ......... *H01L 51/008* (2013.01); *H01L 51/0089* (2013.01); *H01L 51/0091* (2013.01); *H01L 51/5072* (2013.01)

(56) References Cited

U.S. PATENT DOCUMENTS

| | | | |
|---|---|---|---|
| 6,645,645 B1* | 11/2003 | Adachi et al. | 428/690 |
| 6,784,016 B2* | 8/2004 | Long et al. | 438/99 |
| 2002/0045063 A1 | 4/2002 | Kim et al. | |
| 2003/0218418 A9* | 11/2003 | Sato et al. | 313/504 |
| 2008/0143254 A1* | 6/2008 | Yamazaki et al. | 313/504 |

FOREIGN PATENT DOCUMENTS

| | | | | |
|---|---|---|---|---|
| JP | H09-328679 A | * | 12/1997 | ............ C09K 11/06 |
| JP | 2000-030864 A | * | 1/2000 | ............ H05B 33/14 |
| JP | 2002-338957 A | | 11/2002 | |
| WO | WO-01/39234 A2 | | 5/2001 | |

OTHER PUBLICATIONS

Meyer et al. "Metallomesogens: synthesis and properties" J. Mater Chem. vol. 8, No. 6, 1998. pp. 1351-1354.*

English language machine translation of JP H09-328679 A, 1997.*

Lorenze, D., et al., Copper(II) and zinc(II) complexes of 2-(o-hydroxy-phenyl)-benzoxazole and -benzothiazole), Inorg. Nucl. Chem. Letters. 1976, vol. 12, pp. 65-71.

* cited by examiner

COMPOUNDS HAVING ELECTRON TRANSPORT PROPERTIES, THEIR PREPARATION AND USE

CROSS-REFERENCE TO RELATED APPLICATIONS

This application is a national stage application (under 35 U.S.C. §371) of PCT/EP2009/005708, filed Aug. 6, 2009, which claims benefit of British application 0814954.4, filed Aug. 18, 2008.

FIELD OF THE INVENTION

This invention relates to novel compounds, to a method for their preparation and to their use in a layer of an electro-optical or opto-electronic device e.g. in optical light emitting devices e.g. in an electron transport layer of an organic light emitting diode (OLED) device forming part of a flat panel display and/or in lighting or e.g. as an electron transport layer in an electrophotography.

BACKGROUND TO THE INVENTION

Kulkarni et al., Chem. Mater. 2004, 16, 4556-4573 (the contents of which are incorporated herein by reference) have reviewed the literature concerning electron transport materials (ETMs) used to enhance the performance of OLEDs. In addition to a large number of organic materials, they discuss metal chelates including aluminium quinolate, which they explain remains the most widely studied metal chelate owing to its superior properties such as high EA (~−3.0 eV; measured by the present applicants as −2.9 eV) and IP (~−5.95 eV; measured by the present applicants as about −5.7 eV), good thermal stability (Tg~172° C.) and ready deposition of pin-hole-free thin films by vacuum evaporation. Aluminium quinolate remains a preferred material both for use as a host to be doped with various fluorescent or phosphorescent materials to provide an electroluminescent layer and for use as an electron transport layer. It is an object of the invention to provide additional electron transport materials that provide alternatives to aluminium quinolate when used in an electron transport layer e.g. of an OLED and that may in some embodiments provide superior performance in at least some respects e.g. greater current density at a given voltage.

SUMMARY OF THE INVENTION

The invention provides a compound of the formula I, II or III

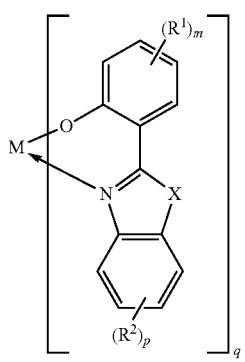

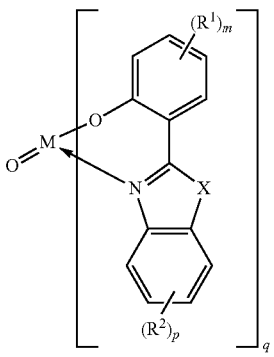

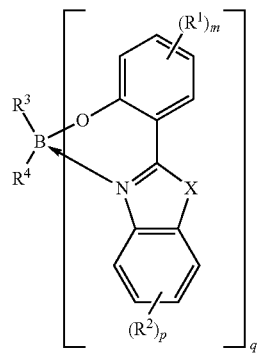

wherein

M represents Li, Na, Mg, Al, Ti, Zr, Hf, Cu, Zn, Si or a lanthanide and in formula II M additionally may be vanadium;

X represents oxygen or sulphur;

m and p are independently 0-4;

q is 1 to 4, depending on the valence of M;

$R^1$ and $R^2$ independently represent $C_1$ to $C_4$ alkyl or alkoxy, fluorine-substituted alkyl or alkoxy, fluoroalkyl, fluoroalkoxy, cycloalkyl or cycloalkoxy, aryl, heteroaryl, fluoro, cyano, aryl or heteroaryl substituted with one or more groups selected from $C_1$ to $C_4$ alkyl or alkoxy, fluorine-substituted alkyl or alkoxy, fluoroalkyl, fluoroalkoxy, fluoro or cyano, or when m or p is 2 to 4 represents fused cycloalkyl, aryl or heteroaryl which in turn may be substituted with one or more groups selected from $C_1$ to $C_4$ alkyl or alkoxy, fluorine-substituted alkyl or alkoxy, fluoroalkyl, fluoroalkoxy, fluoro or cyano; and $R^3$ and $R^4$ independently represent $C_1$ to $C_4$ alkyl, cyclopentyl, cyclohexyl or phenyl or naphthyl which may have one or more groups selected from $C_1$ to $C_4$ alkyl or alkoxy, fluorine-substituted alkyl or alkoxy, fluoroalkyl, fluoroalkoxy, fluoro or cyano.

The invention further provides a composition comprising a compound of any of the formulae I, II or III as set out above and at least one n-dopant and/or electron transport material.

The invention yet further comprises an OLED having a layer comprising a compound of any of the formulae I, II or II as set out above.

The invention further provides an electro-optical or opto-electronic device having a layer comprising a compound of any of the formulae I, II or III as set out above.

BRIEF DESCRIPTION OF THE DRAWINGS

The invention will be further described with reference to the drawings, in which.

DESCRIPTION OF PREFERRED EMBODIMENTS

Figure 1:
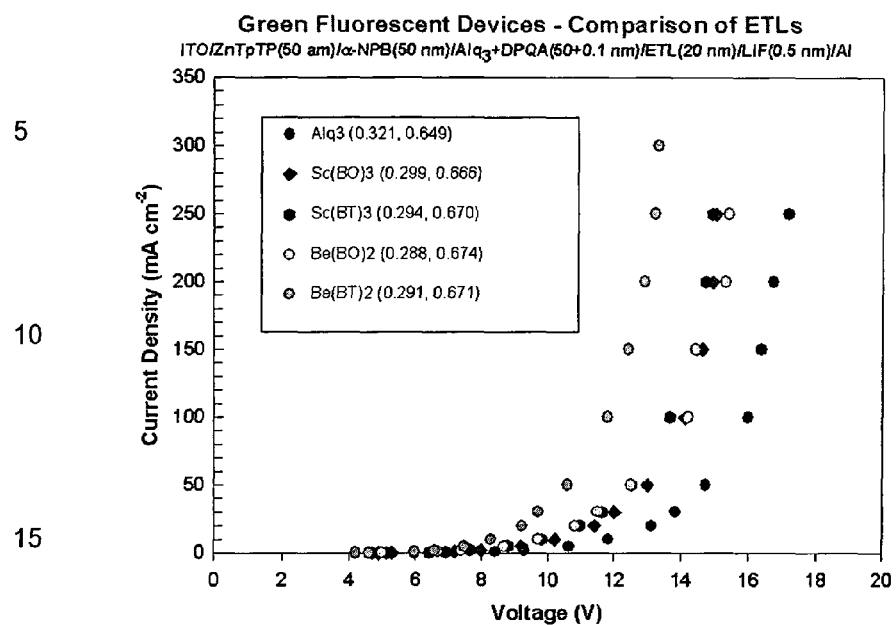
FIGS. 1 to 3 are performance graphs for OLEDs according to the invention and OLEDs having an aluminium quinolate electron transfer layer (reference) and FIG. 4 shows formulae of some compounds incorporated into embodiments of those OLEDs.

As previously explained, the invention comprises a compound of the formula I, II or III

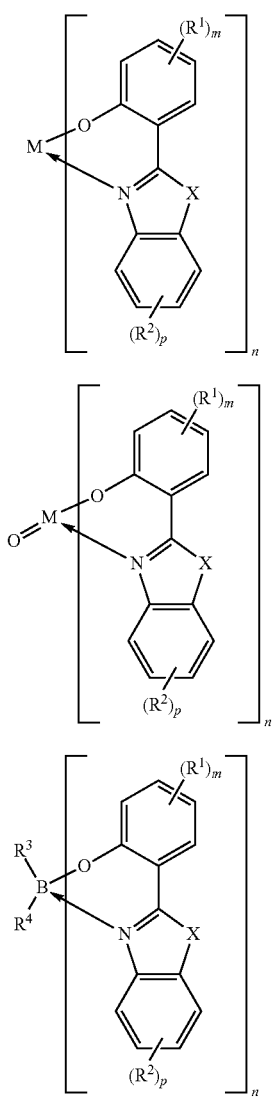

In the above formulae:
M represents any of Li, Na, Mg, Al, Ti, Zr, Hf, Cu, Zn, Si or a lanthanide and in formula II M additionally may be vanadium. By lanthanide is meant any of lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu) together with Yttrium (Y) and scandium (Sc) are sometimes included in the group of rare earth elements;
X represents oxygen or sulphur,
m and p are independently 0 to 4 and in embodiments have the value 1 or 2; and
q is 1 to 4, depending on the valence of M;
$R^1$ and $R^2$ independently represent $C_1$ to $C_4$ alkyl or alkoxy, fluorine-substituted alkyl or alkoxy, fluoroalkyl, fluoroalkoxy, cycloalkyl or cycloalkoxy, aryl, heteroaryl, fluoro, cyano, aryl or heteroaryl substituted with one or more groups selected from $C_1$ to $C_4$ alkyl or alkoxy, fluorine-substituted alkyl or alkoxy, fluoroalkyl, fluoroalkoxy, fluoro or cyano, or when m or p is 2 to 4 represents fused cycloalkyl, aryl or heteroaryl which in turn may be substituted with one or more groups selected from $C_1$ to $C_4$ alkyl or alkoxy, fluorine-substituted alkyl or alkoxy, fluoroalkyl, fluoroalkoxy, fluoro or cyano.

Alkyl includes methyl, ethyl, n-propyl, i-propyl, n-butyl, s-butyl and t-butyl. Alkoxy includes e.g. methoxy. Cycloalkyl includes cyclopentyl and cyclohexyl. Fluoroalkyl includes trifluoromethyl, fluoralkoxy includes trifluoromethoxy. Fused aryl or heteroaryl most commonly comprises, with the illustrated aromatic ring a bicyclic or tricyclic structure, and such bicyclic or tricyclic structures may be present on either or both of the illustrated aromatic rings. $R^3$ and $R^4$ independently represent $C_1$ to $C_4$ alkyl, cyclopentyl, cyclohexyl or phenyl or naphthyl which may have one or more substituents selected from $C_1$ to $C_4$ alkyl or alkoxy, fluorine-substituted alkyl or alkoxy, fluoroalkyl, fluoroalkoxy, fluoro or cyano e.g. t-butyl or phenyl.

Particular ligands include 2-(benzo[d]oxazol-2-yl)phenol, 2-(benzo[d]thiazol-2-yl)phenol, 2-(5-methylbenzo[d]oxazol-2-yl)phenol, 2-(benzo[d]oxazol-2-yl)naphthalen-1-ol, 2-(5-methylbenzo[d]oxazol-2-yl)naphthalen-1-ol, 2-(naphtho[1,2-d]oxazol-2-yl)phenol, 2-(benzo[d]thiazol-2-yl)phenol and 2-(benzo[d]thiazol-2-yl)naphthalen-1-ol. Compounds of formula I, II or III with mixed ligands falling within the definition above are also within the invention.

The term aryl as used herein is defined as a aromatic group comprising 5 to 60 C atoms. The term heteroaryl group as used herein is defined as aromatic group comprising 2 to 60 C atoms and at least one heteroatom, whereby the sum of C atoms and heteroatoms is at least 5. The heteroatoms are preferably selected from Si, N, P, O, S and Se, particularly preferably selected from N, P, O, and S. Both the aryl group and the heteroaryl group can be an monocyclic system, e.g. benzene, pyridine, pyrimidine, and thiophene, or a polycyclic system, e.g. naphtalene, anthracene, phenanthrene, quinoline, isoquinoline, benzothiophene, benzofuran, and indole.

Cell Structure

The OLEDs of the invention are useful inter alia in flat panel displays and in embodiments comprise an anode and a cathode between which is sandwiched a multiplicity of thin layers including an electroluminescent layer, electron injection and/or transport layer(s), hole injection and/or transport layer(s) and optionally ancillary layers. The layers are in embodiments built up by successive vacuum vapour deposition operations, although it may be convenient to form one or more of the layers e.g. the hole injection and hole transport layers by other methods e.g. spin coating or ink jet printing. The devices according to the present invention can also comprise more than two electrodes.

A device comprises in some embodiments a transparent substrate on which are successively formed an anode layer, a hole injector (buffer) layer, a hole transport layer, an electroluminescent layer, an electron transport layer, an electron injection layer and an anode layer which may in turn be laminated to a second transparent substrate. Top emitting OLEDs are also possible in which an aluminium or other metallic substrate carries an ITO layer, a hole injection layer, a hole transport layer, an electroluminescent layer, an electron transport layer, an electron injection layer and an ITO or other transparent cathode, light being emitted through the cathode. A further possibility is an inverted OLED in which a cathode of aluminium or aluminium alloyed with a low work function metal carries successively an electron injection layer, an electron transport layer, an electroluminescent layer, a hole transport layer, a hole injection layer and an ITO or other transparent conductive anode, emission of light being through the anode. If desired a hole blocking layer may be inserted e.g. between the electroluminescent layer and the electron transport layer. OLEDs of the invention include small molecule OLEDs, polymer light emitting diodes (p-OLEDs), OLEDs that emit light by fluorescence, OLEDs that emit light by phosphorescence (PHOLEDs) and OLEDs that emit light by ion fluorescence (rare earth complexes) and include single-colour or multi-colour active or passive matrix displays.

The OLEDs may be of the active matrix type or of the passive matrix type. As well known, in active matrix devices each pixel is controlled by one or more transistors associated with that pixel. A representative active matrix OLED array is described in U.S. Pat. No. 5,929,474 (Huang, Motorola) the contents of which are incorporated herein by reference. That specification describes an active matrix organic light emitting device array comprising:

(a) a semiconductor substrate having an array area defined thereon;

(b) a plurality of field effect transistors, each including first and second current carrying terminals and a control terminal, formed in the array area on the semiconductor substrate in rows and columns, each of the rows including a row bus coupled to the first current carrying terminal of each field effect transistor in the row, and each of the columns including a column bus coupled to the control terminal of each field effect transistor in the column;

(c) a planarizing layer of insulating material positioned over the plurality of field effect transistors in the array area and defining a substantially planar surface;

(d) a plurality of contact pads formed on the planar surface of the planarizing layer in the array area in rows and columns, each contact pad of the plurality of contact pads associated with one field effect transistor of the plurality of field effect transistors and coupled to the second current carrying terminal of the associated field effect transistor by a conductor formed through the planar layer;

(e) a plurality of layers of organic material sequentially formed in overlying relationship on the contact pads in the array area so as to define an organic light emitting device on each contact pad with each contact pad operating as a first terminal of an overlying organic light emitting device; and (f) electrical and light conducting material positioned in overlying relationship over the layers of organic material in the array area and operating as a common second terminal of the organic light emitting devices. Further references describing active matrix devices are EP-A-0717446 (Tang et al., Kodak) and WO 99/65012 (Knapp et al., Philips) the disclosures of which are incorporated herein by reference. Choice of active or passive matrix driving may affect the selection of electrode materials, but need not fundamentally affect the choice of materials for the layers between the electrodes.

Anode

In many embodiments the anode is formed by a layer of tin oxide or indium tin oxide coated onto glass or other transparent substrate. Other materials that may be used include antimony tin oxide and indium zinc oxide. If desired a modified anode may be produced e.g. by subsequently treating the ITO surface with oxygen plasma, and then conditioned as a modified anode by decomposing $CHF_3$ gas in a plasma treatment chamber to deposit an ~1-nm-thick layer of $CF_x$. In active matrix embodiments the anode may be a high work function metal or alloy e.g. gold or platinum or may be crystalline, polycrystalline, continuous grain or amorphous silicon which may be p-doped.

Hole Injection Materials

A single layer may be provided between the anode and the electroluminescent material, but in many embodiments there are at least two layers one of which is a hole injection layer (buffer layer) and the other of which is a hole transport layer, the two layer structure offering in some embodiments improved stability and device life, see U.S. Pat. No. 4,720,432 (VanSlyke et al., Kodak). The hole injection layer may serve to improve the film formation properties of subsequent organic layers and to facilitate the injection of holes into the hole transport layer.

Suitable materials for the hole injection layer which may be of thickness e.g. 0.1 to 200 nm depending on material and cell type include hole-injecting porphyrinic compounds—see U.S. Pat. No. 4,356,429 (Tang, Eastman Kodak) e.g. zinc phthalocyanine copper phthalocyanine and ZnTpTP, whose formula is set out below:

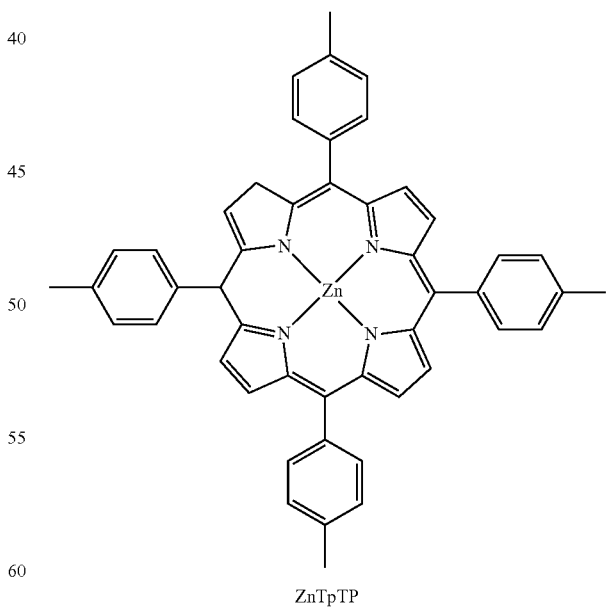

ZnTpTP

Particularly good device efficiencies, turn/on voltages and/or lifetimes may be obtained where the hole injection layer is ZnTpTP. A further material that may be used is hexacyanohexaazatriphenylene (CHATP) of structure:

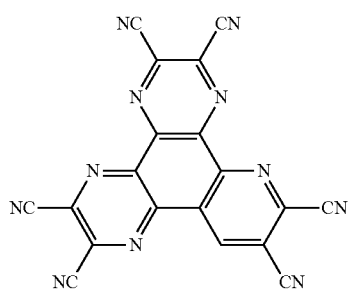 [SMILES: N#Cc1cc2c(nc1C#N)c1nc(C#N)c(C#N)nc1c1nc(C#N)c(C#N)nc21]

The hole injection layer may also be a fluorocarbon-based conductive polymer formed by plasma polymerization of a fluorocarbon gas—see U.S. Pat. No. 6,208,075 (Hung et al; Eastman Kodak), a triarylamine polymer—see EP-A-0891121 (Inoue et al., TDK Corporation) or a phenylenediamine derivative—see EP-A-1029909 (Kawamura et al., Idemitsu) or the materials described in U.S. Pat. No. 6,436,559 (Ueno, Canon) and U.S. Pat. No. 6,720,573 (Se-Hwan, LG Chemical Co., Ltd.). It may also be a solution-processable hole injecting polymer e.g. PEDOT/PSS (poly-3,4-ethylene-dioxythiophene doped with poly(styrenesulfonate) or a block copolymer of PEDOT and a flexible polymer such as a polyether, polysiloxane, polyester, or polyacrylate. Methods of applying such materials include solution processing methods, e.g. spin coating, printing through a mask and ink jet printing e.g. of a relatively dilute solution where thin hole injection layers are desired. The hole injection material may also be an aromatic amine as described in US 2008/0102311 A1 such as N,N'-diphenyl-N,N'-di(3-tolyl)benzidine (=4,4'-bis[N-3-methylphenyl]-N-phenylamino)biphenyl, NPD) (U.S. Pat. No. 5,061,569), N,N'-bis(N,N'-diphenyl-4-aminophenyl)-N,N-diphenyl-4,4'-diamino-1,1'-biphenyl (TPD 232), and 4,4',4"-tris[3-methylphenyl)phenylamino]-triphenylamine (MT-DATA) (JP Heisei 4 (1992) 308688) or an aromatic amine as described in U.S. Pat. No. 7,399,537 B2 (HIL 1), US 2006/0061265 A1, EP 1661888 B1 (HIL2), and JP 08292586 A (HIL 3).

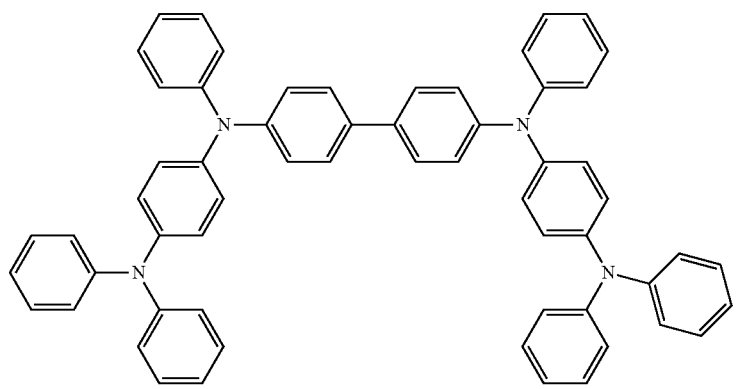

TPD232

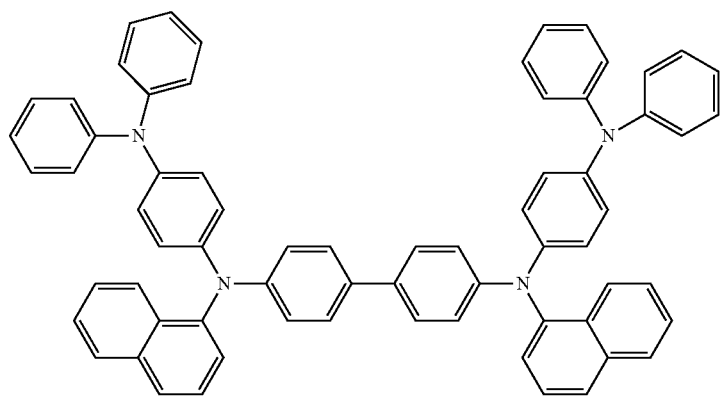

HIL 1

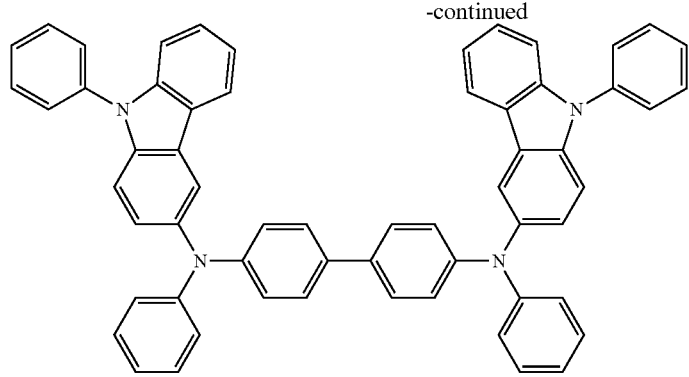

HIL 2

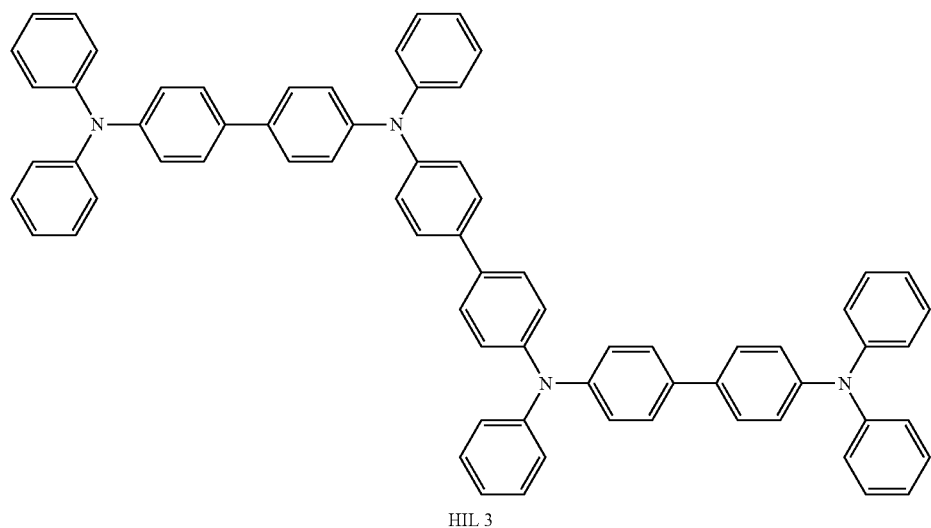

HIL 3

Hole-transport Materials

Hole transport layers which may be used are in some embodiments preferably of thickness 20 to 200 nm.

One class of hole transport materials comprises polymeric materials that may be deposited as a layer by solution processing methods e.g. spin coating or ink jet printing. Such polymeric hole-transporting materials include poly(N-vinyl-carbazole) (PVK), polythiophenes, polypyrrole, and polyaniline. Other hole transporting materials are conjugated polymers e.g. poly(p-phenylenevinylene) (PPV) and copolymers including PPV. Other preferred polymers are: poly(2,5 dialkoxyphenylene vinylenes e.g. poly(2-methoxy-5-(2-methoxypentyloxy-1,4-phenylene vinylene), poly(2-methoxypentyloxy)-1,4-phenylenevinylene), poly(2-methoxy-5-(2-dodecyloxy-1,4-phenylenevinylene) and other poly(2,5 dialkoxyphenylenevinylenes) with at least one of the alkoxy groups being a long chain solubilising alkoxy group; polyfluorenes and oligofluorenes; polyphenylenes and oligophenylenes; polyanthracenes and oligoanthracenes; and polythiophenes and oligothiophenes.

A further class of hole transport materials comprises sublimable small molecules. For example, aromatic tertiary amines provide a class of preferred hole-transport materials, e.g. aromatic tertiary amines having at least two aromatic tertiary amine moieties (e.g. those based on biphenyl diamine or of a "starburst" configuration).

For example, aromatic amines may be used of the general formulae (i)-(xii) below:

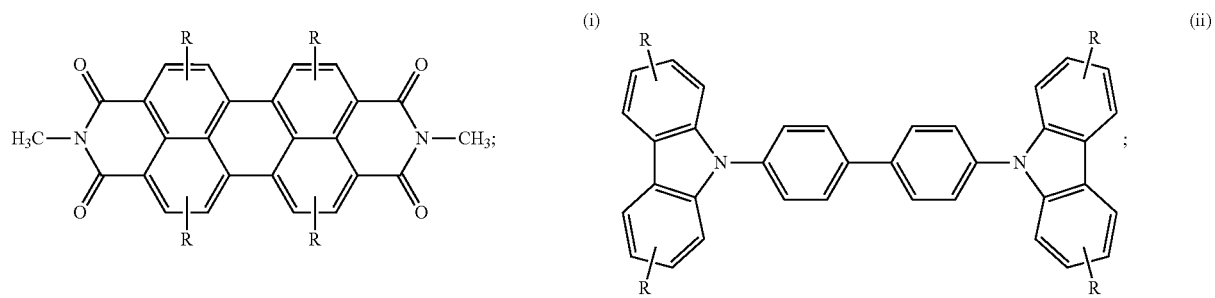

-continued
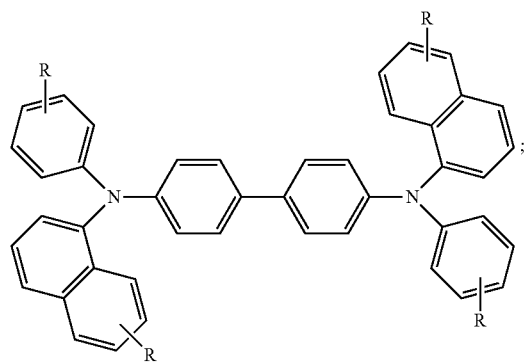
(iii)
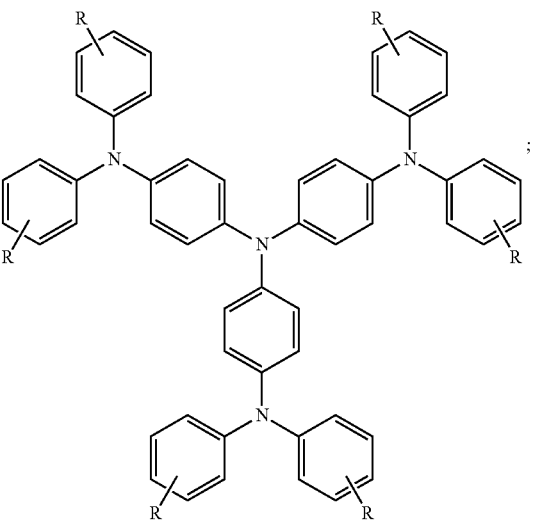
(iv)
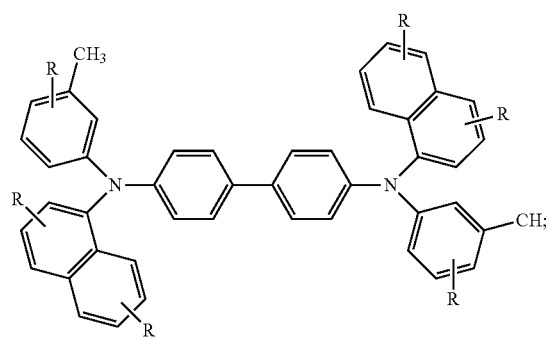
(v)
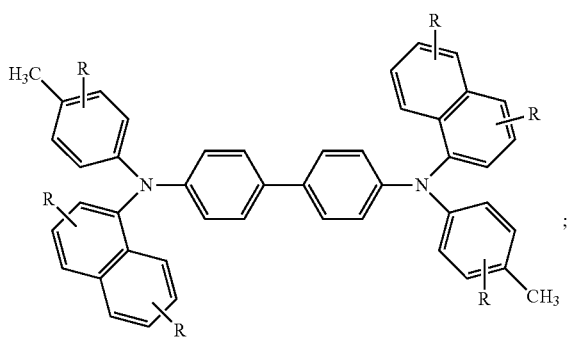
(vi)
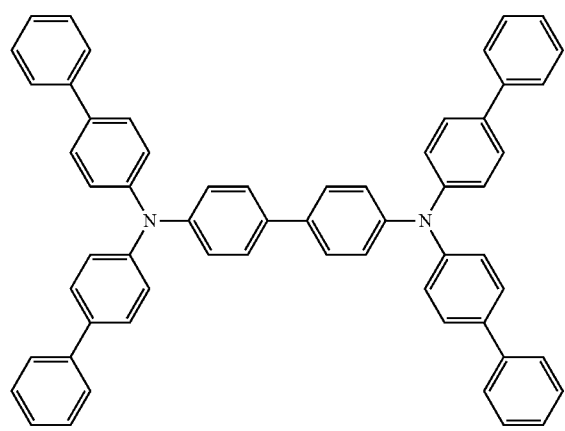
(vii)
HTL1
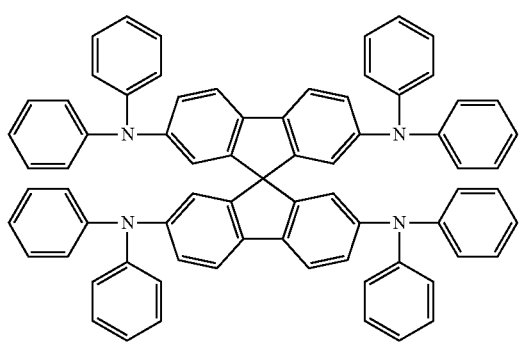
(viii)
HTL2

-continued
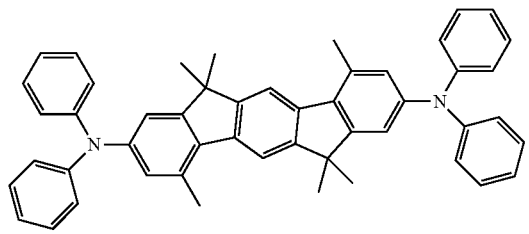
HTL3
(ix)
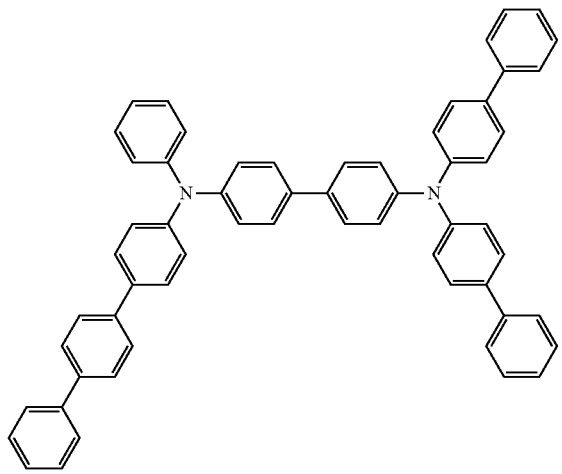
HTL4
(x)
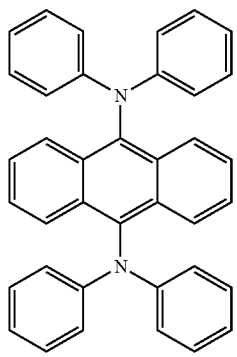
HTL5
(xi)
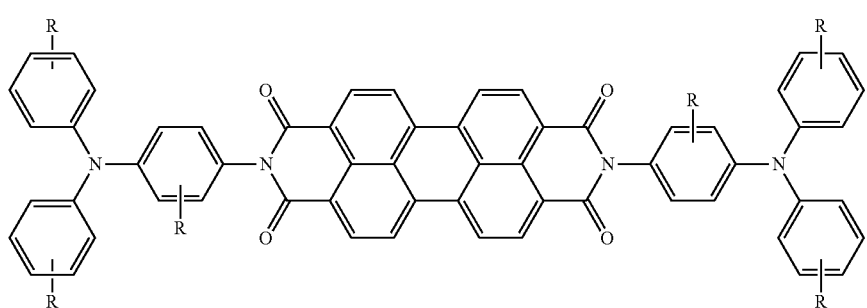
(xii)

wherein
the groups R in any of the formulae in (i) to (xii) can be the same or different and are selected from hydrogen; substituted and unsubstituted aliphatic groups; substituted and unsubstituted aromatic, heterocyclic and polycyclic ring structures; halogens; and thiophenyl groups;

and wherein in formula (i) the methyl groups may be replaced by $C_1$ to $C_4$ alkyl or monocyclic or polycyclic aryl or heteroaryl which may be further substituted e.g. with alkyl, aryl or arylamino.

Further hole transport materials comprise

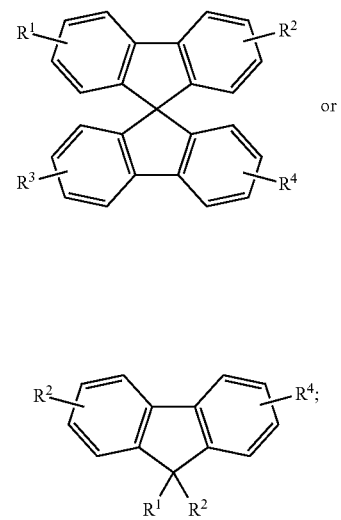

wherein
the groups $R^1$ to $R^4$ when appearing in either of the above formulae can be the same or different and are selected from hydrogen; substituted and unsubstituted aliphatic groups; substituted and unsubstituted aromatic, heterocyclic and polycyclic ring structures; halogens; and thiophenyl groups.

Particular preferred hole-transport materials are aromatic tertiary amines including at least two aromatic tertiary amine moieties (e.g. those based on biphenyl diamine or of a "starburst" configuration) of which the following are representative:

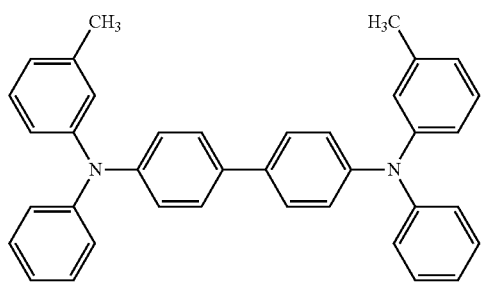

TPD
Tg (°C.) 61
$\mu h\ (cm^2\ V^{-1}\ s^{-1})\ 1 \times 10^{-3}$

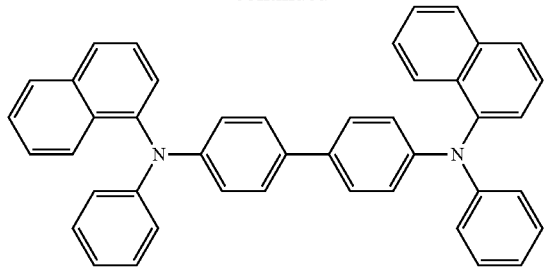

α-NBP
Tg (°C.) 98
$\mu h\ (cm^2\ V^{-1}\ s^{-1})\ 1 \times 10^{-4}$

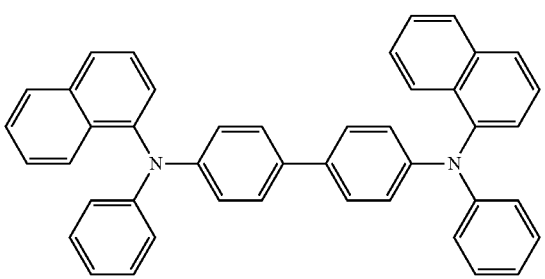

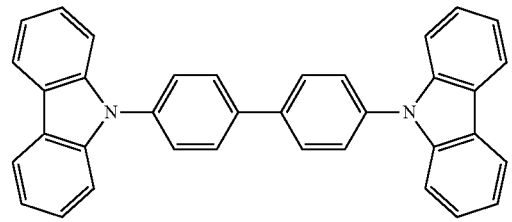

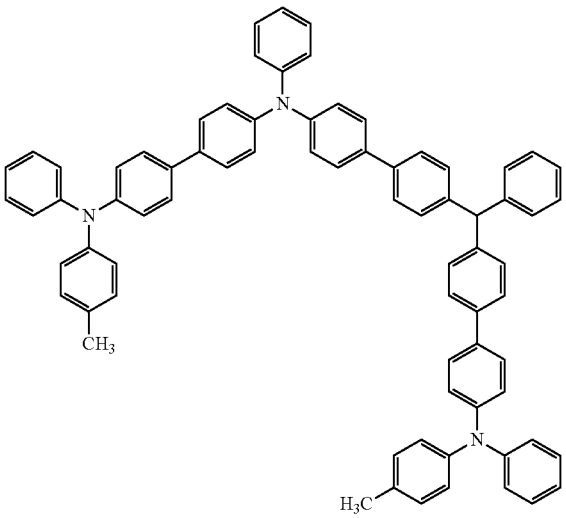

-continued

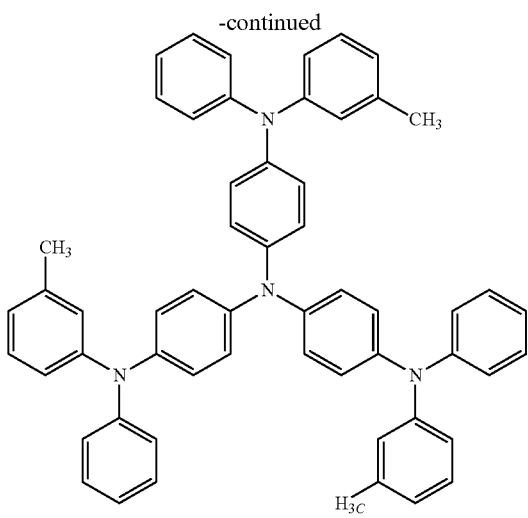

m-MTDATA; Tg (°C.) 75; μh (cm$^2$ V$^{-1}$ s$^{-1}$) 2.7×10$^{-5}$

A further possible material is 4,4',4''-tris(carbazolyl)-triphenylamine (TCTA) which is a hole transport material with a wider band gap than α-NPB and which can in some embodiments assist in confining excitation to the emissive layer.

It further includes spiro-linked molecules which are aromatic amines e.g. spiro-TAD (2,2',7,7'-tetrakis-(diphenylamino)-spiro-9,9'-bifluorene).

A further class of small molecule hole transport materials is disclosed in WO 2006/061594 (Kathirgamanathan et al) and is based on diamino dianthracenes. Such compounds include:
9-(10-(N-(naphthalen-1-yl)-N-phenylamino)anthracen-9-yl)-N-(naphthalen-1-yl)-N-phenylanthracen-10-amine;
9-(10-(N-biphenyl-N-2-m-tolylamino)anthracen-9-yl)-N-biphenyl-N-2-m-tolylamino-anthracen-10-amine; and
9-(10-(N-phenyl-N-m-tolylamino)anthracen-9-yl)-N-phenyl-N-m-tolylanthracen-10-amine.

The hole transport layer may be p-doped e.g. with a an acceptor-type organic molecule e.g. tetrafluorotetracyanoquinodimethane (F$_4$-TCNQ) e.g. it may be starburst m-MTDATA doped with F$_4$-TCNQ.

Electroluminescent Materials

In principle any electroluminescent material may be used, including molecular solids which may be fluorescent dyes e.g. perylene dyes, metal complexes e.g. Alq$_3$, so-called "blue" aluminium quinolates of the type Alq$_2$L where q represents a quinolate and L represents a mono-anionic aryloxy ligand e.g. bis(2-methyl-8-quinolinolato)(4-phenyl-phenolato)Al(III), Ir(III)L$_3$, rare earth chelates e.g. Tb(III) complexes, dendrimers and oligomers e.g. sexithiophene, or polymeric emissive materials. The electroluminescent layer may comprise as luminescent material a metal quinolate, an iridium, ruthenium, osmium, rhodium, palladium or platinum complex, a boron complex or a rare earth complex.

One preferred class of electroluminescent materials comprises host materials doped with one or more dyes or complexes which may be fluorescent, phosphorescent or ion-phosphorescent (rare earth). The term "electroluminescent device" includes electrophosphorescent devices.

Preferably the host is doped with a minor amount of a fluorescent or phosphorescent material as a dopant, preferably in an amount of 0.01 to 25% by weight of the doped mixture. As discussed in U.S. Pat. No. 4,769,292 (Tang et al., Kodak), the contents of which are included by reference, the presence of the fluorescent or phosphorescent material permits a choice from amongst a wide latitude of wavelengths of light emission. In particular, as disclosed in U.S. Pat. No. 4,769,292 by blending with the organo metallic complex a minor amount of a fluorescent material capable of emitting light in response to hole-electron recombination, the hue of the light emitted from the luminescent zone, can be modified. In theory, if a host material and a fluorescent material could be found for blending which have exactly the same affinity for hole-electron recombination, each material should emit light upon injection of holes and electrons in the luminescent zone. The perceived hue of light emission would be the visual integration of both emissions. However, since imposing such a balance of host material and fluorescent materials is limiting, it is preferred to choose the fluorescent material so that it provides the favoured sites for light emission. When only a small proportion of fluorescent material providing favoured sites for light emission is present, peak intensity wavelength emissions typical of the host material can be entirely eliminated in favour of a new peak intensity wavelength emission attributable to the fluorescent material.

While the minimum proportion of fluorescent or phosphorescent material sufficient to achieve this effect varies, in no instance is it necessary to employ more than about 10 mole percent fluorescent or phosphorescent material, based on the host material and seldom is it necessary to employ more than 1 mole percent of the fluorescent or phosphorescent material. On the other hand, limiting the fluorescent or phosphorescent material present to extremely small amounts, in some embodiments less than about 10$^{-3}$ mole percent, based on the host material, can result in retaining emission at wavelengths characteristic of the host material. Thus, by choosing the proportion of a fluorescent or phosphorescent material capable of providing favoured sites for light emission, either a full or partial shifting of emission wavelengths can be realized. This allows the spectral emissions of the EL devices to be selected and balanced to suit the application to be served. In the case of fluorescent dyes, amounts in some embodiments are 0.01 to 5 wt %, for example 2 to 3 wt %. In the case of phosphorescent dyes amounts in some embodiments are 0.1 to 15 wt %. In the case of ion phosphorescent materials amounts in some embodiments are 0.01 to 25 wt % or up to 100 wt %.

Choosing fluorescent materials capable of providing favoured sites for light emission necessarily involves relating the properties of the fluorescent material to those of the host material. The host can be viewed as a collector for injected holes and electrons with the fluorescent material providing the molecular sites for light emission. One important relationship for choosing a fluorescent material capable of modifying the hue of light emission when present in the host is a comparison of the reduction potentials of the two materials. The fluorescent materials demonstrated to shift the wavelength of light emission have exhibited a less negative reduction potential than that of the host. Reduction potentials, measured in electron volts, have been widely reported in the literature along with varied techniques for their measurement. Since it is a comparison of reduction potentials rather than their absolute values which is desired, it is apparent that any accepted technique for reduction potential measurement can be employed, provided both the fluorescent and host reduction potentials are similarly measured. A preferred oxidation and reduction potential measurement techniques is reported by R. J. Cox, Photographic Sensitivity, Academic Press, 1973, Chapter 15.

A second important relationship for choosing a fluorescent material capable of modifying the hue of light emission when present in the host is a comparison of the band-gap potentials of the two materials. The fluorescent materials demonstrated to shift the wavelength of light emission have exhibited a lower band gap potential than that of the host. The band gap potential of a molecule is taken as the potential difference in electron volts (eV) separating its ground state and first singlet state. Band gap potentials and techniques for their measurement have been widely reported in the literature. The band gap potentials herein reported are those measured in electron volts at an absorption wavelength which is bathochromic to the absorption peak and of a magnitude one tenth that of the magnitude of the absorption peak. Since it is a comparison of band gap potentials rather than their absolute values which is desired, it is apparent that any accepted technique for band gap measurement can be employed, provided both the fluorescent and host band gaps are similarly measured. One illustrative measurement technique is disclosed by F. Gutman and L. E. Lyons, *Organic Semiconductors*, Wiley, 1967, Chapter 5.

With host materials which are themselves capable of emitting light in the absence of the fluorescent material, it has been observed that suppression of light emission at the wavelengths of emission characteristics of the host alone and enhancement of emission at wavelengths characteristic of the fluorescent material occurs when spectral coupling of the host and fluorescent material is achieved. By "spectral coupling" it is meant that an overlap exists between the wavelengths of emission characteristic of the host alone and the wavelengths of light absorption of the fluorescent material in the absence of the host. Optimal spectral coupling occurs when the emission wavelength of the host is within ±25 nm of the maximum absorption of the fluorescent material alone. In practice advantageous spectral coupling can occur with peak emission and absorption wavelengths differing by up to 100 nm or more, depending on the width of the peaks and their hypsochromic and bathochromic slopes. Where less than optimum spectral coupling between the host and fluorescent materials is contemplated, a bathochromic as compared to a hypsochromic displacement of the fluorescent material produces more efficient results.

Useful fluorescent materials are those capable of being blended with the host and fabricated into thin films satisfying the thickness ranges described above forming the luminescent zones of the EL devices of this invention. While crystalline organometallic complexes do not lend themselves to thin film formation, the limited amounts of fluorescent materials present in the host permit the use of fluorescent materials which are alone incapable of thin film formation. Preferred fluorescent materials are those which form a common phase with the host. Fluorescent dyes constitute a preferred class of fluorescent materials, since dyes lend themselves to molecular level distribution in the host. Although any convenient technique for dispersing the fluorescent dyes in the host can be used preferred fluorescent dyes are those which can be vacuum vapour deposited along with the host materials.

One class of host materials comprises metal complexes e.g. metal quinolates such as lithium quinolate, aluminium quinolate, titanium quinolate, zirconium quinolate or hafnium quinolate which may be doped with fluorescent materials or dyes as disclosed in patent application WO 2004/058913.

In the case of hosts which comprise quinolates e.g. aluminum quinolate or "blue" quinolates, see e.g. J. C. Deaton et al., *Inorg. Chim. Acta* (2007), doi:10.1016/j.ica.2007.07.008, the contents of which are incorporated herein by reference:

(a) the compounds below, for example, can serve as red dopants:

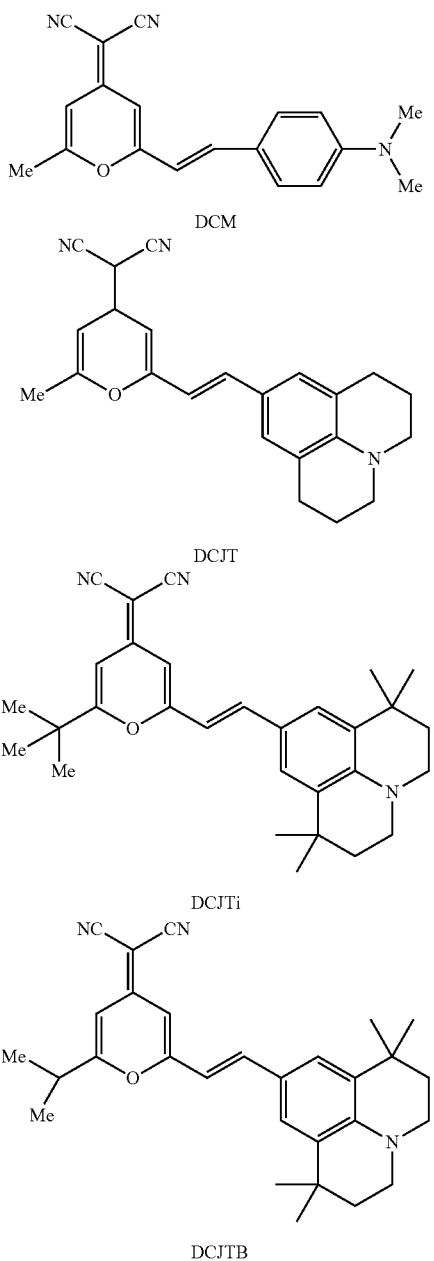

(b) the compounds below, for example can serve as green dopants:

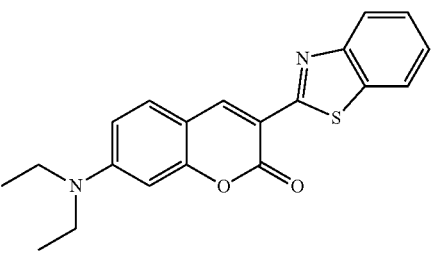

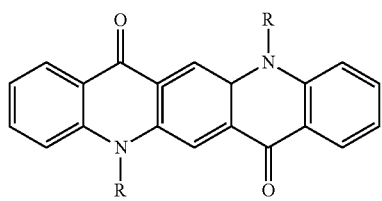

wherein

R is $C_1$ to $C_4$ alkyl, monocyclic aryl, bicyclic aryl, monocyclic heteroaryl, bicyclic heteroaryl, aralkyl or thienyl, preferably phenyl; and (c) for biphenyloxy aluminium bis-quinolate ($BAlQ_2$) or aluminium quinolate the compounds perylene and 9-(10-(N-(naphthalen-8-yl)-N-phenylamino)anthracen-9-yl)-N-(naphthalen-8-yl)-N-phenylanthracen-10-amine can serve as a blue dopants.

Another preferred class of hosts is small molecules incorporating conjugated aromatic systems with e.g. 4 to 10 aryl or heteroaryl rings which may bear substituents e.g. alkyl (especially methyl), alkoxy and fluoro and which may also be doped with fluorescent materials or dyes.

An example of a system of the above kind is a blue-emitting material based on the following compound (Compound H) as host

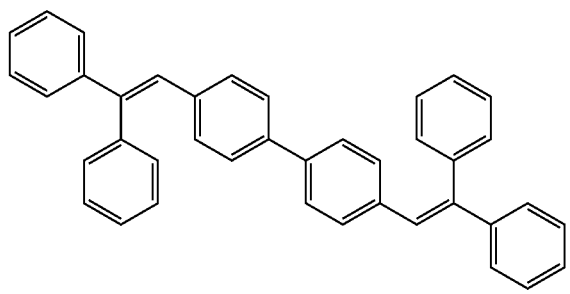

H and perylene or 9-(10-(N-(naphthalen-8-yl)-N-phenylamino) anthracen-9-yl)-N-(naphthalen-8-yl)-N-phenylanthracen-10-amine as dopant. Further examples of host materials which are small aromatic molecules are shown below:

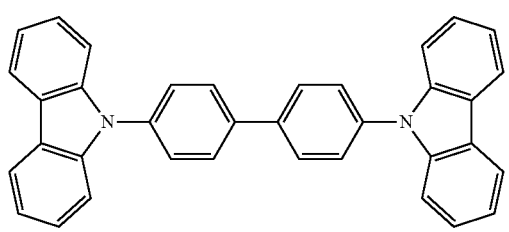

CPB

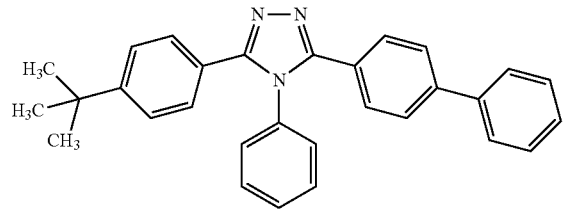

TAZ

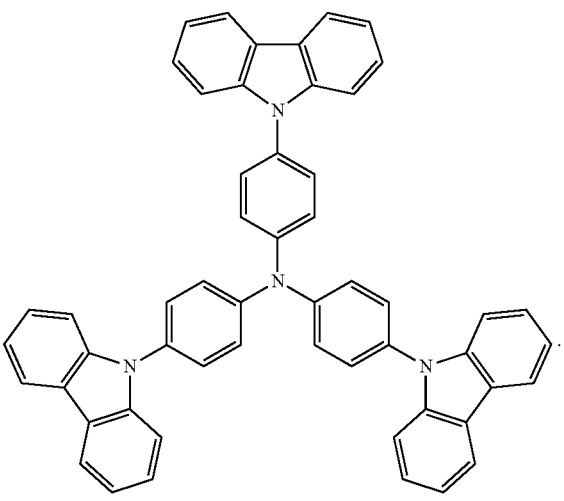

TCTA 2,9-Bis(2-thiophen-2-yl-vinyl)-[1,10] phenanthroline may, as explained above, may be used as host in the electroluminescent layer or may be present on its own.

Blue-emitting materials may be based on an organic host (e.g. a conjugated aromatic compound as indicated above) and diarylamine anthracene compounds disclosed in WO 2006/090098 (Kathirgamanathan et al.) as dopants. For example, CBP may be doped with blue-emitting substituted anthracenes inter alia 9,10-bis(-4-methylbenzyl)-anthracene, 9,10-bis-(2,4-dimethylbenzyl)-anthracene, 9,10-bis-(2,5-dimethylbenzyl)-anthracene, 1,4-bis-(2,3,5,6-tetramethylbenzyl)-anthracene, 9,10-bis-(4-methoxybenzyl)-anthracene, 9,10-bis-(9H-fluoren-9-yl)-anthracene, 2,6-di-t-butylanthracene, 2,6-di-t-butyl-9,10-bis-(2,5-dimethylbenzyl)-anthracene, 2,6-di-t-butyl-9,10-bis-(naphthalene-1-ylmethyl)-anthracene.

Further blue-emitting materials may employ TCTA as host and it may be doped with the blue phosphorescent materials set out below, see WO 2005/080526 (Kathirgamanathan et al.):

Blue Phosphorescent Materials
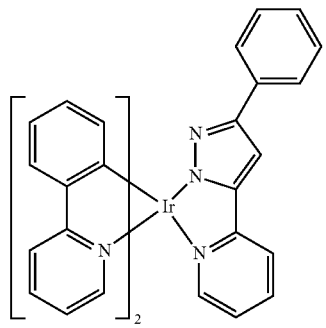
λmax 495 nm (DCM)
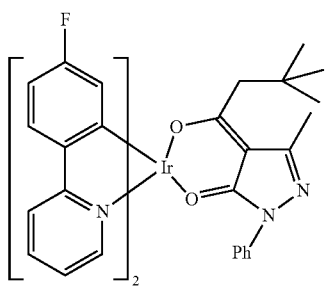
λmax 493 nm (DCM)
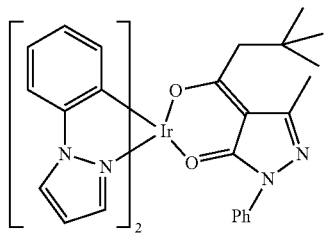
λmax 485 nm (DCM)
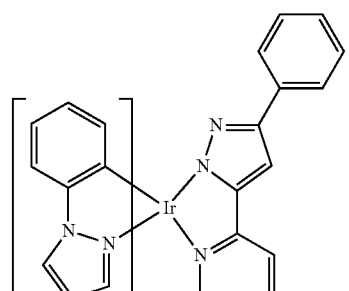
λmax 485 nm (DCM)
-continued
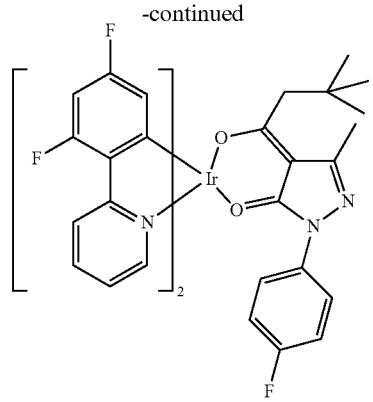
λmax 484 nm (DCM)
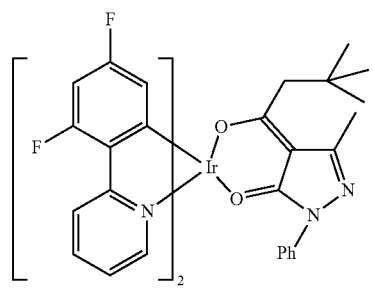
λmax 483 nm (DCM)
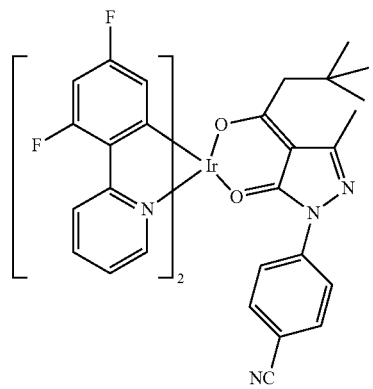
λmax 480 nm (DCM)
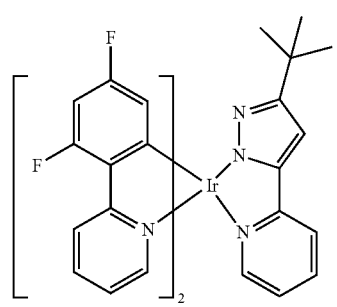
λmax 479 nm (DCM)

-continued
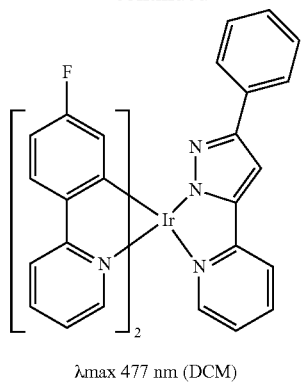
λmax 477 nm (DCM)
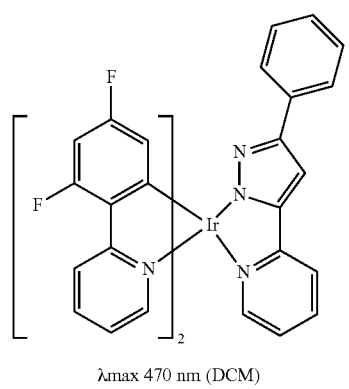
λmax 470 nm (DCM)
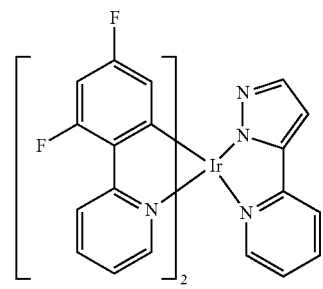
λmax 469, 493 nm (DCM)
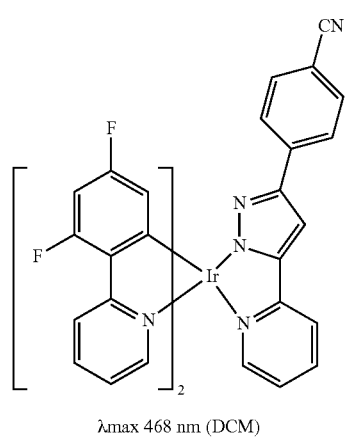
λmax 468 nm (DCM)
-continued
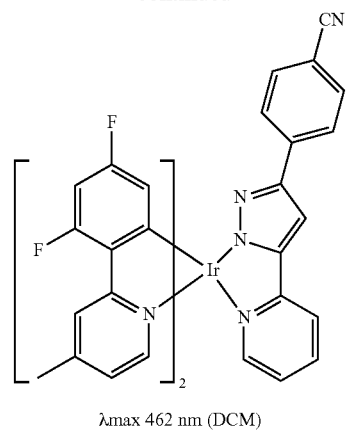
λmax 462 nm (DCM)
Examples of green phosphorescent materials that may be employed with CBP or TAZ are set out below (see WO 2005/080526):
Green Phosphorescent Materials
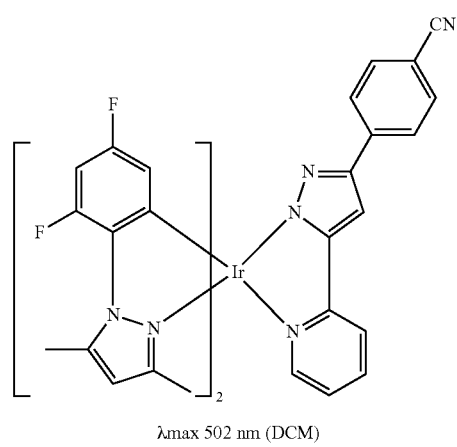
λmax 502 nm (DCM)
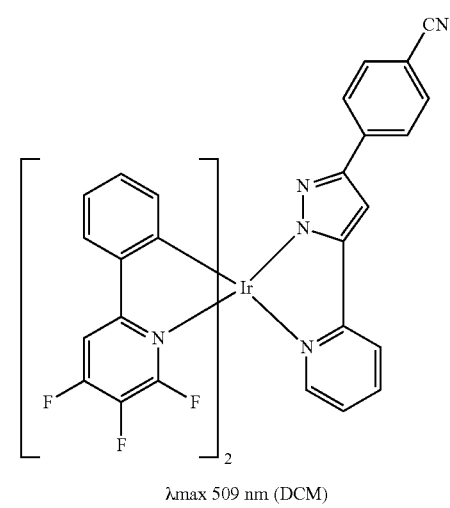
λmax 509 nm (DCM)

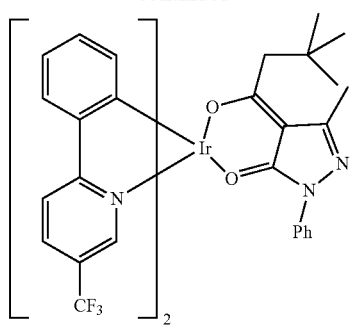
λmax 520 nm (DCM)
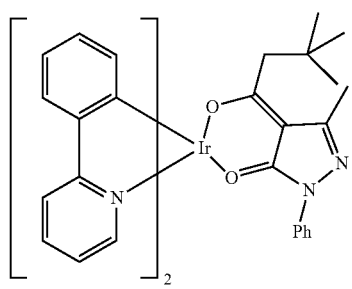
λmax 526 nm (DCM)
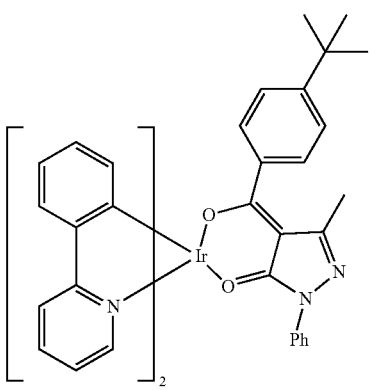
λmax 528 nm (DCM)
Examples of red phosphorescent materials that may be employed with CBP or TAZ are set out below (see WO 2005/080526):
Red Phosphorescent Materials
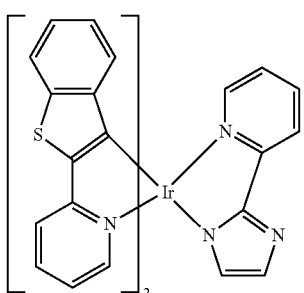
λmax 596 nm (DCM)
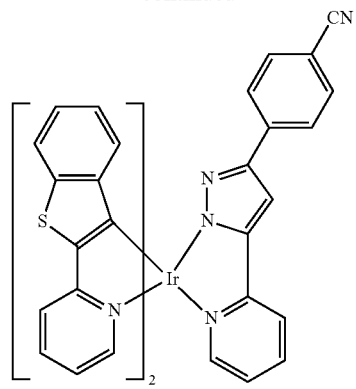
λmax 596 nm (DCM)
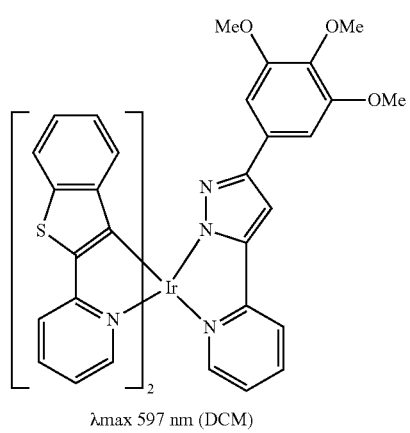
λmax 597 nm (DCM)
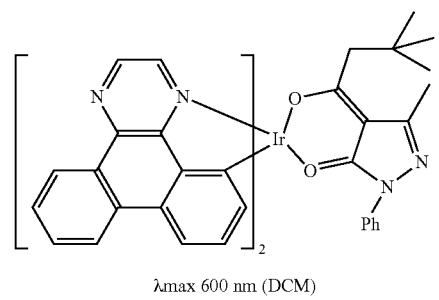
λmax 600 nm (DCM)
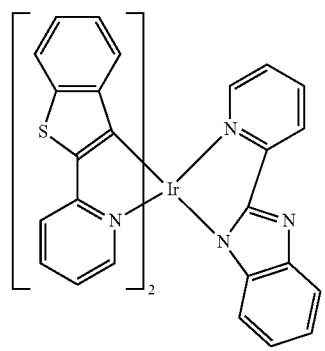
λmax 604 nm (DCM)

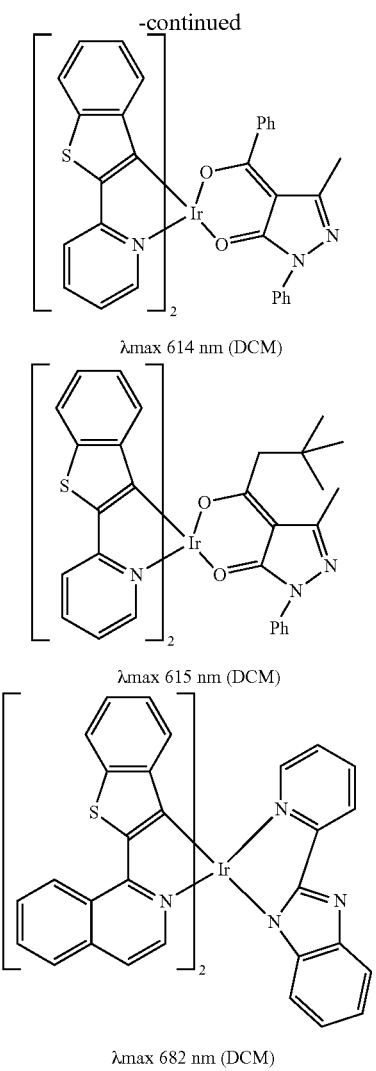

λmax 614 nm (DCM)

λmax 615 nm (DCM)

λmax 682 nm (DCM)

As further dopants, fluorescent laser dyes are recognized to be particularly useful fluorescent materials for use in the organic EL devices of this invention. Dopants which can be used include diphenylacridine, coumarins, perylene and their derivatives. Useful fluorescent dopants are disclosed in U.S. Pat. No. 4,769,292. One class of preferred dopants is coumarins. The following are illustrative fluorescent coumarin dyes known to be useful as laser dyes:

FD-1 7-Diethylamino-4-methylcoumarin,
FD-2 4,6-Dimethyl-7-ethylaminocoumarin,
FD-3 4-Methylumbelliferone,
FD-4 3-(2'-Benzothiazolyl)-7-diethylaminocoumarin,
FD-5 3-(2'-Benzimidazolyl)-7-N,N-diethylaminocoumarin,
FD-6 7-Amino-3-phenylcoumarin,
FD-7 3-(2'-N-Methylbenzimidazolyl)-7-N,Ndiethylaminocoumarin,
FD-8 7-Diethylamino-4-trifluoromethylcoumarin,
FD-9 2,3,5,6-1H,4H-Tetrahydro-8-methylquinolazino[9,9a,1-gh]coumarin,
FD-10 Cyclopenta[c]julolindino[9,10-3]-11H-pyran-11-one,
FD-11 7-Amino-4-methylcoumarin,
FD-12 7-Dimethylaminocyclopenta[c]coumarin,
FD-13 7-Amino-4-trifluoromethylcoumarin,
FD-14 7-Dimethylamino-4-trifluoromethylcoumarin,
FD-15 1,2,4,5,3H,6H,10H-Tetrahydro-8-trifluoromethyl[1]benzopyrano[9,9a,1-gh]quinolizin-10-one,
FD-16 4-Methyl-7-(sulfomethylamino)coumarin sodium salt,
FD-17 7-Ethylamino-6-methyl-4-trifluoromethylcoumarin,
FD-18 7-Dimethylamino-4-methylcoumarin,
FD-19 1,2,4,5,3H,6H,10H-Tetrahydro-carbethoxy[1]benzopyrano[9,9a,1-gh]quinolizino-10-one,
FD-20 9-Acetyl-1,2,4,5,3H,6H,10H-tetrahydro[1]benzopyrano[9,9a,1-gh]quinolizino-10-one,
FD-21 9-Cyano-1,2,4,5,3H,6H,10H-tetrahydro[1]benzopyrano[9,9a,1-gh]quinolizino-10-one,
FD-22 9-(t-Butoxycarbonyl)-1,2,4,5,3H,6H,10H-tetrahyro[1]-benzopyrano-[9,9a,1-gh]quinolizino-10-one,
FD-23 4-Methylpiperidino[3,2-g]coumarin,
FD-24 4-Trifluoromethylpiperidino[3,2-g]coumarin,
FD-25 9-Carboxy-1,2,4,5,3H,6H,10H-tetrahydro[1]benzopyrano[9,9a,1-gh]quinolizino-10-one,
FD-26 N-Ethyl-4-trifluoromethylpiperidino[3,2-g].

Other dopants include salts of bis benzene sulphonic acid (require deposition by spin-coating rather than sublimation) such as (C)

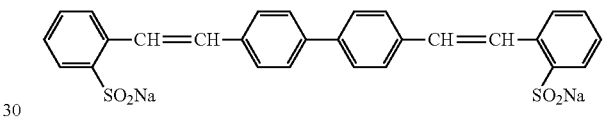

and perylene and perylene derivatives and dopants. Other dopants are dyes such as the fluorescent 4-dicyanomethylene-4H-pyrans and 4-dicyanomethylene-4H-thiopyrans, e.g. the fluorescent dicyanomethylenepyran and thiopyran dyes. Useful fluorescent dyes can also be selected from among known polymethine dyes, which include the cyanines, complex cyanines and merocyanines (i.e. tri-, tetra- and poly-nuclear cyanines and merocyanines), oxonols, hemioxonols, styryls, merostyryls, and streptocyanines. The cyanine dyes include, joined by a methine linkage, two basic heterocyclic nuclei, such as azolium or azinium nuclei, for example, those derived from pyridinium, quinolinium, isoquinolinium, oxazolium, thiazolium, selenazolium, indazolium, pyrazolium, pyrrolium, indolium, 3H-indolium, imidazolium, oxadiazolium, thiadioxazolium, benzoxazolium, benzothiazolium, benzoselenazolium, benzotellurazolium, benzimidazolium, 3H- or 1H-benzoindolium, naphthoxazolium, naphthathiazolium, naphthoselenazolium, naphthotellurazolium, carbazolium, pyrrolopyridinium, phenanthrothiazolium, and acenaphthothiazolium quaternary salts. Other useful classes of fluorescent dyes are 4-oxo-4H-benz-[d,e]anthracenes and pyrylium, thiapyrylium, selenapyrylium, and telluropyrylium dyes.

Further blue-emitting materials are disclosed in the following patents, applications and publications, the contents of which are incorporated herein by reference:

U.S. Pat. No. 5,141,671 (Bryan, Kodak)—Aluminium chelates containing a phenolato ligand and two 8-quinolinolato ligands.

WO 00/32717 (Kathirgamanathan)—Lithium quinolate which is vacuum depositable, and other substituted quinolates of lithium where the substituents may be the same or different in the 2,3,4,5,6 and 7 positions and are selected from alky, alkoxy, aryl, aryloxy, sulphonic acids, esters, carboxylic acids, amino and amido groups or are aromatic, polycyclic or heterocyclic groups.

US 2006/0003089 (Kathirgamanathan)—Lithium quinolate made by reacting a lithium alkyl or alkoxide with 8-hydroxyquinoline in acetonitrile.

Misra A. et al U.R.S.I. GA 2005, "Synthesis and characterisation of blue organic electroluminescent bis(2-methyl 8-quinolinolato) (triphenyl Siloxy) aluminium for OLEDs applications"; see the following website: http://www.ursi.org/Proceedings/ProcGA05/pdf/D04.5(01720).pdf—Blue organic electroluminescent material bis-(2-methyl 8-quinolinolato) (triphenyl siloxy)aluminium (III) vacuum depositable at 1×10−5 Torr.

WO 03/006573 (Kathirgamanathan et al)—Metal pyrazolones.

WO 2004/084325 (Kathirgamanathan et al)—Boron complexes.

WO 2005/080526 (Kathirgamanathan et al)—Blue phosphorescent iridium-based complexes.

Ma et al., Chem. Comm. 1998, 2491-2492 Preparation and crystal structure of a tetranuclear zinc(II) compound [$Zn_4O(AlD)_6$] with 7-azaindolate as a bridging ligand. Fabrication of inter alia a single-layer LED by vacuum deposition of this compound (<200° C., $2\times10^{-6}$ Torr) onto a glass substrate coated with indium-tin oxide to form a thin homogeneous film was reported.

Further electroluminescent materials which can be used include metal quinolates such as aluminium quinolate, lithium quinolate, titanium quinolate, zirconium quinolate, hafnium quinolate etc.

Many further electroluminescent materials that may be used are disclosed in WO 2004/050793 (pyrazolones), WO 2004/058783 (diiridium metal complexes), WO 2006/016193 (dibenzothiophenyl metal complexes) and WO 2006/024878 (thianthrene metal complexes); see also WO 2006/040593 the contents of which are incorporated herein by reference. Rare earth chelates, in particular may be employed as green and red emitters. Furthermore, there may be used as electroluminescent materials conducting polymers e.g. phenylene vinylene polymers, fluorene homopolymers and copolymers, phenylene polymers, as indicated below:

Conducting Polymers

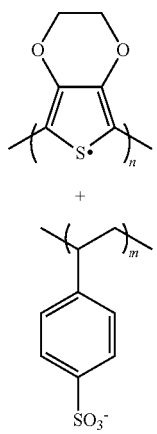

PEDOT-PSS
($\sigma = 1$ S cm$^{-1}$)

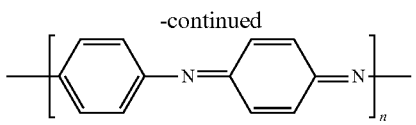

Polyaniline (PANI)
($\sigma = 1$-$10$ S cm$^{-1}$)

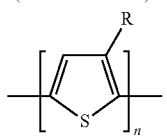

Polythiophine (PT)
($\sigma = 1$-$500$ S cm$^{-1}$)

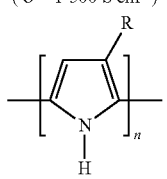

Polypyrrole (PPy)
($\sigma = 1$-$100$ S cm$^{-1}$)

Mixed host materials have also been disclosed in the literature and may be used in OLEDs devices according to the invention. Various references disclose additives and mixed hosts for OLED's in an attempt to further improve properties. Jarikov et al., J. Appl. Phys., 100, 014901 (2006) discloses flat and rigid polycyclic aromatic hydrocarbons (PAHs) as LEL additives e.g. perylene. Jarikov et al. further report J. Appl. Phys., 100, pp. 094907-094907-7 (2006) perylene derivatives as light-emitting-layer (LEL) additives in organic light-emitting diodes (OLEDs). These molecules readily form emissive aggregates when added to the LEL. Addition of these polycyclic aromatic hydrocarbons increases the half-life ($t_{50}$) of undoped and doped OLEDs by 30 to 150 times e.g. in an $Alq_3$+dibenzo[b,k]perylene mixed host. The authors yet further report in J. Appl. Phys., 102, 104908 (2007) a synergistic effect of a lifetime-extending light-emitting-layer (LEL) additive and improved electron injection and transport in organic light-emitting diodes (OLEDs). Di-(2-naphthyl) perylene (DNP) serves as a LEL additive said to extend the operating lifetime of OLEDs by over two orders of magnitude. Using 2-phenyl-9,10-di(2-naphthyl)anthracene (PADN) as an electron-transport layer (ETL) and a separate layer of 4,7-diphenyl-1,10-phenanthroline (BPhen) as an electron-injection layer (EIL) the authors claimed to have significantly improved electron delivery into the charge recombination zone relative to traditional ETL made of tris (8-quinolinolate)aluminium (Alq). See also U.S. Pat. No. 7,175,922 (Jarikov et al) the disclosure of which is incorporated herein by reference. J. C. Deaton et al (supra) disclose an α-NPB host with a "blue" aluminium quinolate as co-host and an iridium dopant. Very good yields were obtained with low concentrations of dopant for phosphorescent devices and it was found that the mixed host device provided increased power efficiency. It was hypothesized that the explanation was a reduction in the energy barrier to inject holes into the emissive layer by mixing the hole-transporting NPB having an ionization potential of 5.40 eV into the dominantly electron-transporting "blue" aluminium quinolate, having a higher ionization potential of 6.02 eV.

U.S. Pat. No. 6,392,250 (Aziz et al, the disclosure of which is incorporated herein by reference.) discloses organic light emitting devices comprising a mixed region comprising a mixture of a hole transport material e.g. an aromatic tertiary amine, an electron transport material e.g. a quinolate and a dopant material. For example N,N'-di-1-naphthyl-N,N'-diphenyl-1,1'-biphenyl-1,1'-biphenyl-4,4'-diamine (NPB), and tris(8-hydroxyquinoline)aluminium (Alq$_3$) may be used as the hole transport material and the electron transport material, respectively and N,N'-dimethylquinacridone (DMQ), 5,6,11,12-tetraphenylnapthacene (Rubrene), and Nile-red dye (available from Aldrich Chemicals of Milwaukee, Wis.) may be used as dopants.

US 2002/0074935 (Kwong et al) also discloses devices with an emissive layer containing PtOEP or bis(benzothienyl-pyridinato-NAC)Iridium(III) (acetylacetonate) as a dopant and equal proportions of NPB and Alq as host materials. It is explained that the mixed host electroluminescent mixed layer serves to substantially reduce the accumulation of charge that is normally present at the heterojunction interface of heterostructure devices, thereby reducing organic material decomposition and enhancing device stability and efficiency.

In US 2004/0155238 (Thompson et al.) a light emitting layer of the OLED device contains a wide band gap inert host matrix in combination with a charge carrying material and a phosphorescent emitter. The charge carrying compound can transport holes or electrons, and it is selected so that charge carrying material and phosphorescent emitter transport charges of opposite polarity.

M. Furugori et al. in US 2003/0141809 disclose phosphorescent devices where a host material is mixed with another hole- or electron transporting material in the light emitting layer. The document discloses that devices utilizing plural host compounds show higher current and higher efficiencies at a given voltage.

T. Igarashi et al. in WO 2004/062324 disclose phosphorescent devices with the light emitting layer containing at least one electron transporting compound, at least one hole transporting compound and a phosphorescent dopant.

WO 2006/076092 (Kondakova et al., the contents of which are also incorporated herein by reference) discloses OLED device comprising a cathode, an anode, and located therebetween a light emitting layer (LEL) comprising at least one hole transporting co-host e.g. an aromatic tertiary amine such as 4,4'-Bis[N-(I-naphthyl)-N-phenylamino]biphenyl (NPB), 4,4'-Bis[N-(I-naphthyl)-N-(2-naphthyl)amino]biphenyl (TNB), 4,4'-Bis[N-(3-methylphenyl)-N-phenylamino-]biphenyl (TPD), 4,4'-Bis-diphenylamino-terphenyl or 2,6,2',6'-tetramethyl-N,N,N',N'-tetraphenyl-benzidine and at least one electron transporting co-host e.g. a substituted 1,2,4-triazole such as 3-phenyl-4-(1-naphtyl)-5-phenyl-1,2,4-triazole or a substituted 1,3,5-triazine such as 2,4,6-tris(diphenylamino)-1,3,5-triazine, 2,4,6-tricarbazolo-1,3,5-triazine, 2,4,6-tris(N-phenyl-2-naphthylamino)-1,3,5-triazine, 2,4,6-tris(N-phenyl-1-naphthylamino)-1,3,5-triazine and 4,4',6,6'-tetraphenyl-2,2'-bi-1,3,5-triazine together with a phosphorescent emitter, wherein the triplet energy of each of the co-host materials is greater than the triplet energy of the phosphorescent emitter, and further containing an exciton blocking layer comprising a hole transporting material with triplet energy greater or equal to 2.5 eV adjacent the emitting layer on the anode side, which may be a substituted triarylamine e.g. 4,4',4"-tris[(3-methylphenyl)phenylamino]triphenylamine (MTDATA), 4,4',4"-tris(N,N-diphenyl-amino)triphenylamine (TDATA), N,N-bis[2,5-dimethyl-4-[(3-methylphenyl)-phenylamino]phenyl]-2,5-dimethyl-N'-(3-methylphenyl)-N'-phenyl-1,4-benzenediamine. The devices are said to exhibit improved efficiency and reduced drive voltage.

U.S. Pat. No. 7,045,952 (Lu, Universal Display Corporation) discloses an organic light emissive device comprising an emissive region disposed between and electrically connected to an anode and a cathode, wherein the emissive region comprises (i) a first single-host emissive layer, comprising a first host material, and (ii) a mixed-host emissive layer in direct contact with the first single-host emissive layer, wherein the mixed-host emissive layer comprises the first host material, and a second host material, and wherein the first single-host emissive layer and the mixed-host emissive layer each further comprise a phosphorescent emissive material.

Electron Transport Material

The compounds of the invention may be the totality, or substantially the totality of the electron transport layer. They may also be a component of a mixture of co-deposited materials which comprises a compound as set out above. The layer may be doped e.g. with a fluorescent or phosphorescent dye or ion fluorescent material e.g. as described above in relation to the electroluminescent layer, e.g. in amounts of 0.01-25 wt % based on the weight of the doped mixture. Other dopants include metals which can provide high brightness at low voltage. Additionally or alternatively, the compound as defined above may be used in admixture with another electron transport material. Such materials may include complexes of metals in the trivalent or pentavalent state which should further increase electron mobility and hence conductivity. The compound defined above may be mixed with a quinolate of a metal of group 1, 2, 3, 13 or 14 of the periodic table, e.g. lithium quinolate or zinc quinolate. Additionally the electron transport material may be n-doped e.g. with donor-type organic molecules. Preferably the compound set out above comprises at least 30 wt % of the electron transport layer, more preferably at least 50 wt %.

Electron Injection Material

The following electron injection materials of the above mentioned general formula have been prepared—for preparative details see the Examples:

| Name (My Ref.) | Structure | E.A. (%) Theory | E.A. (%) Found | M. Pt. DSC Peak (° C.) | Tg (° C.) |
|---|---|---|---|---|---|
| Be(BO)$_2$ | 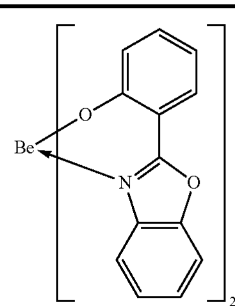 | C = 72.72<br>H = 3.76<br>N = 6.52 | C = 72.62<br>H = 3.60<br>N = 6.48 | 268 | 112 |

-continued

| Name (My Ref.) | Structure | E.A. (%) Theory | E.A. (%) Found | M. Pt. DSC Peak (° C.) | Tg (° C.) |
|---|---|---|---|---|---|
| Be(BT)$_2$ | 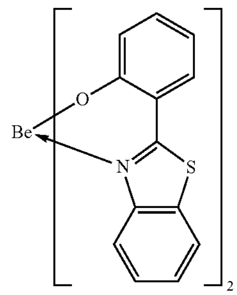 | C = 67.66<br>H = 3.49<br>N = 6.07 | C = 67.65<br>H = 3.35<br>N = 6.07 | 330 | No Tg |
| Be(5MeBO)$_2$ | 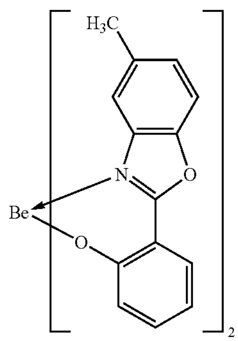 | C = 73.51<br>H = 4.41<br>N = 6.12 | C = 73.38<br>H = 4.30<br>N = 6.12 | 292 (288) | ~115 |
| Sc(BO)$_3$ | 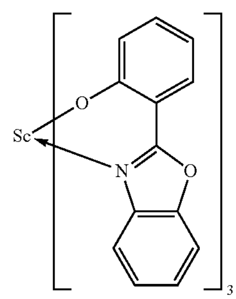 | C = 69.34<br>H = 3.58<br>N = 6.22 | C = 69.37<br>H = 3.52<br>N = 6.36 | 339 | No Tg |
| Sc(BT)$_3$ | 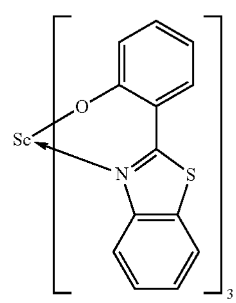 | C = 64.72<br>H = 3.34<br>N = 5.81 | C = 64.55<br>H = 3.33<br>N = 6.04 | 395 | No Tg |
| Mg(BO)$_2$ | 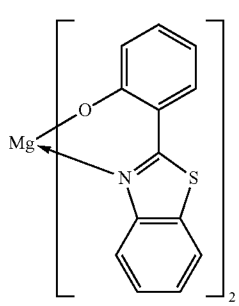 | C = 70.22<br>H = 3.63<br>N = 6.30 | C = 70.19<br>H = 3.58<br>N = 6.30 | Above 400 | No Tg |

-continued

| Name (My Ref.) | Structure | E.A. (%) Theory | E.A. (%) Found | M. Pt. DSC Peak (° C.) | Tg (° C.) |
|---|---|---|---|---|---|
| Zr(BO)₄ | | C = 67.01<br>H = 3.46<br>N = 6.01 | C = 66.83<br>H = 3.39<br>N = 5.78 | 328 | No Tg |
| Zr(BT)₄ | | | | 391<br>(unsublimed) | No Tg |
| Zr(5MeBO)₄ | | C = 68.07<br>H = 4.08<br>N = 5.67 | C = 68.20<br>H = 3.87<br>N = 5.68 | 351 | No Tg |
| Ba(BO)₂ | | C = 55.99<br>H = 2.89<br>N = 5.02 | C = 54.38<br>H = 3.05<br>N = 4.75 | 227 | No Tg |
| Ba(BT)₂ | | C = 52.94<br>H = 2.73<br>N = 4.75 | C = 52.06<br>H = 2.67<br>N = 4.55 | 408 | No Tg |

| Name (My Ref.) | Structure | E.A. (%) Theory | Found | M. Pt. DSC Peak (° C.) | Tg (° C.) |
|---|---|---|---|---|---|
| Hf(BO)$_4$ | 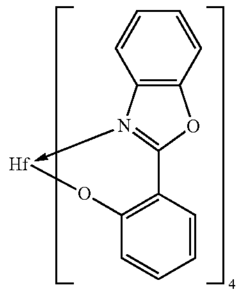 | | | ~280 (unsublimed) | No Tg |
| Hf(BT)$_4$ | 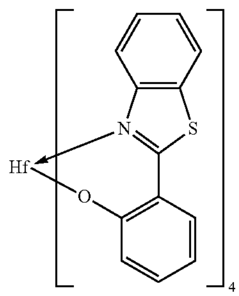 | | | ~320 (unsublimed) | No Tg |
| Cu(BO)$_2$ | 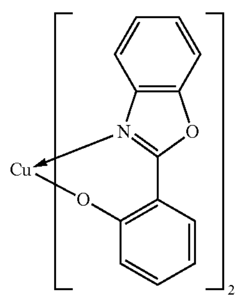 | C = 64.53 H = 3.33 N = 5.79 | C = 64.17 H = 3.39 N = 5.70 | 329 | No Tg |
| Y(BO)$_3$ | 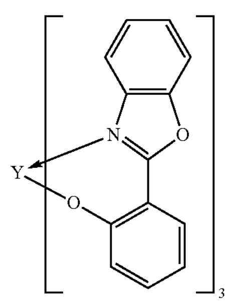 | C = 65.10 H = 3.36 N = 5.84 | C = 63.69 H = 3.43 N = 5.57 | Not Observed | No Tg |
| Y(BT)$_3$ | 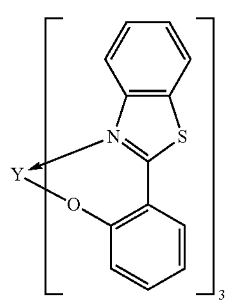 | C = 61.04 H = 3.15 N = 5.47 | C = 61.06 H = 3.15 N = 6.05 | Not Observed | No Tg |

-continued

| Name (My Ref.) | Structure | E.A. (%) Theory | Found | M. Pt. DSC Peak (° C.) | Tg (° C.) |
|---|---|---|---|---|---|
| La(BO)$_3$ | 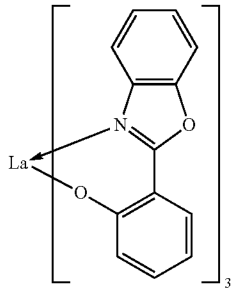 | | | | No Tg |
| La(BT)$_3$ | 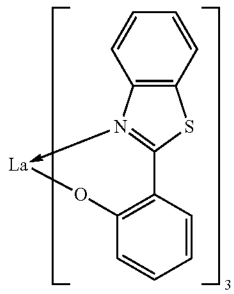 | | | | No Tg |
| VO(BO)$_2$ | 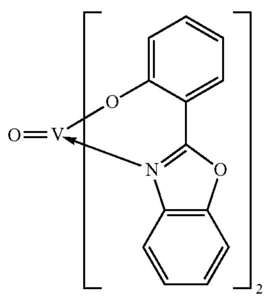 | C = 64.08<br>H = 3.31<br>N = 5.75 | C = 64.33<br>H = 3.31<br>N = 5.75 | 316 | No Tg |
| VO(BT)$_2$ | 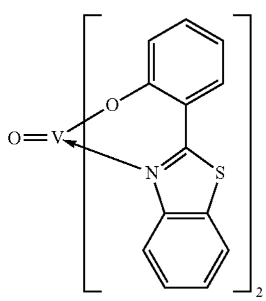 | C = 60.11<br>H = 3.10<br>N = 5.39 | C = 60.29<br>H = 3.11<br>N = 5.59 | 402 | No Tg |
| Al(BO)$_3$ | 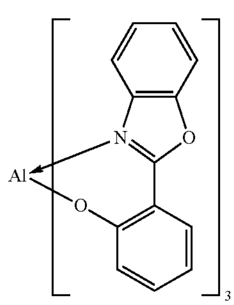 | C = 71.23<br>H = 3.68<br>N = 6.39 | C = 71.24<br>H = 3.55<br>N = 6.36 | 298 | ~145 |

-continued

| Name (My Ref.) | Structure | E.A. (%) Theory | Found | M. Pt. DSC Peak (° C.) | Tg (° C.) |
|---|---|---|---|---|---|
| Yb(BO)₃ | | C = 58.28<br>H = 3.01<br>N = 5.23 | C = 58.27<br>H = 2.95<br>N = 5.27 | 413 | No Tg |
| (BO—Ph—DPB) | | C = 80.02<br>H = 4.83<br>N = 3.73 | C = 80.12<br>H = 4.87<br>N = 3.80 | 195 | 59 |
| (BT—Ph—DPB) | | C = 76.74<br>H = 4.64<br>N = 3.58<br>S = 8.19 | C = 76.82<br>H = 4.60<br>N = 3.64<br>S = 8.30 | 222 | 76 |
| (5MeBO—Np—DPB) | | C = 82.02<br>H = 5.05<br>N = 3.19 | C = 82.04<br>H = 5.08<br>N = 3.28 | 276 | 89 |
| (BT—Np—DPB) | | C = 78.92<br>H = 4.57<br>N = 3.17<br>S = 7.27 | C = 78.79<br>H = 4.62<br>N = 3.20<br>S = 7.23 | 269 | No Tg |

Any known electron injection material may be used, LiF being typical. Other possibilities include $BaF_2$, $CaF_2$ and $CsF_2$. A further class of electron injectors comprises sublimable or coatable e.g. spin-coatable small molecules with electron injection properties. Embodiments of a layer of small molecule electron injection material are about 0.3 to 2 nm in thickness, in some particular embodiments about 0.3 nm in thickness and in other embodiments about 0.5 to 1 nm in thickness and preferably has a work function of less than magnesium 3.7 eV, this being regarded for present purposes as a low work function. In some embodiments the electron injection material may be doped with a low work function metal e.g. lithium, potassium or caesium. In the case of a lithium-based small molecule electron injection material, doping may be with metallic lithium.

Metal quinolates can lower the work function of the cathode, enable the electroluminescent device to operate at a lower voltage and improve the lifetime and performance of the device. In some embodiments quinolates and derivatives thereof have been found superior to the previously used lithium fluoride. They have significantly lower evaporation temperatures, as is apparent from the table below (q represents quinolate):

| Material | Evaporation Temperature/° C. | Vacuum Pressure/Pa | Evaporation Rate/Å s$^{-1}$ |
|---|---|---|---|
| Liq | 320 | ≤5 × 10$^{-5}$ | 1.0 |
| LiF | 580 | ≤5 × 10$^{-5}$ | 0.1 |

Suitable metal quinolates include the alkali metal quinolates and the alkaline earth quinolates. Preferred metal quinolates have the formula

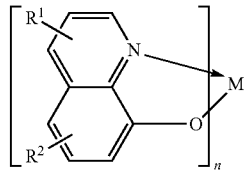

(I)

wherein
M is a metal (in embodiments lithium);
n is the valence state of M when complexed with quinolate; and
$R^1$ and $R^2$ which may be the same or different are selected from $C_1$ to $C_4$ alkyl and substituted or unsubstituted monocyclic or polycyclic aryl or heteroaryl, aralk-($C_1$ to $C_4$)-yl or aryloxy.

Lithium quinolate and lithium 2-methylquinolate are preferred compounds and are preferably the result of reaction between a lithium alkyl or alkoxide with substituted or unsubstituted 8-hydroxy quinoline in a solvent which comprises acetonitrile. Lithium quinolates made as described above are of high purity and readily sublimable.

The electron injection layer deposited direct onto the cathode may alternatively comprise a compound of the formula

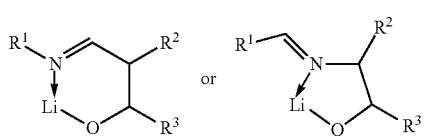

wherein
$R^1$ is a 1 to 5 ring aryl (including polycyclic aryl or aryl-substituted polycyclic aryl), aralkyl or heteroaryl group which may be substituted with one or more $C_1$ to $C_4$ alkyl or alkoxy substituents; and
$R^2$ and $R^3$ together form a 1 to 5 ring aryl (including polycyclic or aryl-substituted polycyclic aryl), aralkyl or heteroaryl group which may be substituted with one or more $C_1$ to $C_4$ alkyl or alkoxy substituents. A compound of the above formula may be used alone or in combination with another electron injection material e.g. a quinolate such as lithium or zirconium quinolate. The Schiff base preferably comprises at least 30 wt % of the electron injection layer, more preferably at least 50 wt %.

In the formula set out above, $R^1$ may be polycyclic aryl e.g. naphthyl, anthracenyl, tetracenyl, pentacenyl or a perylene or pyrene compound or may have up to 5 aromatic rings arranged in a chain e.g. biphenyl. It is preferably phenyl or substituted phenyl. $R^2$ and $R^3$ together may form the same groups as $R^1$ and are preferably phenyl or substituted phenyl. Where substituents are present they may be methyl, ethyl, propyl or butyl, including t-butyl substituted, or may be methoxy, ethoxy, propoxy or butoxy including t-butoxy substituted. Particular compounds include

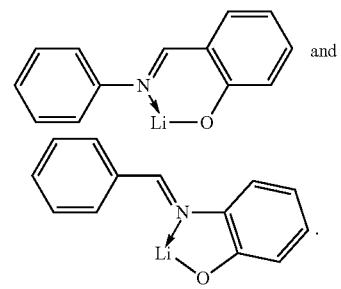

Lithium compounds whose formulae are set out above are believed from MS measurements to be capable of forming cluster compounds or oligomers in which 2 to 8 molecules of formula as set out above are associated e.g. in the form of trimeric, tetrameric, hexameric or octomeric oligomers. It is believed that such lithium compounds may in some embodiments associate in trimeric units having a core structure which has alternating Li and O atoms in a 6-membered ring, and that these trimeric units may further associate in pairs. The existence of such structures in lithium quinolate has been detected by crystallography, see Begley et al., Hexakis(μ-quinolin-8-olato)hexalithium (I): a centrosymmetric doubly stacked trimer, Acta Cryst. (2006), E62, m1200-m1202, the disclosure of which is incorporated herein by reference. It is also believed that formation of oligomeric structures of this type imparts a greater covalent character to the Li—O bonds which may be responsible for the volatility of many of the compounds of the invention which enables them to be deposited at relatively low temperatures by vacuum sublimation. However, other structures may also be possible e.g. cubic structures.

Cathode

The cathode on which there is the layer of electron injection material is in some embodiments a low work function metal. The metal electrode may consist of a plurality of metal layers; for example a higher work function metal such as aluminium deposited on the substrate and a lower work function metal such as calcium or lithium or caesium deposited on the higher work function metal.

The work function of some metals are listed below in Table 1

TABLE 1

| Metal | Work Function eV* |
|---|---|
| Li | 2.9 |
| Na | 2.4 |
| K | 2.3 |
| Cs | 1.9 |
| Ba | 2.5 |
| Ca | 2.9 |
| Nb | 2.3 |
| Zr | 4.05 |
| Mg | 3.66 |
| Al | 4.2 |
| Cu | 4.6 |
| Ag | 4.64 |
| Zn | 3.6 |
| Sc | 3.5 |

*Handbook of Chemistry and Physics

In many embodiments, aluminium is used as the cathode either on its own or alloyed with elements such as magnesium or silver, although in some embodiments other cathode materials e.g. calcium, may be employed. In an embodiment the cathode may comprise a first layer of alloy e.g. Li—Ag, Mg—Ag or Al—Mg closer to the electron injection or electron transport layer and a second layer of pure aluminium further from the electron injection or electron transport layer. In further embodiments the cathode material may be Ag or MgAg or MgIn. Cathode materials may also be on transparent plate materials which may be of glass or may be of plastics which may be rigid or flexible and may be optically transparent As regards plastics substrates, rigid or flexible transparent plastics materials may be used, preferably materials which are dimensionally stable, impermeable to water (including water vapour) of relatively high Tg. PEN is a preferred material, other materials that may be used including PES, PEEK and PET. The plastics may be coated with a conductive film and may also have a barrier coating to improve resistance to moisture which may be encountered under working conditions e.g. atmospheric moisture. In yet further embodiments the cathode may be crystalline, polycrystalline, continuous grain or amorphous silicon which may be n-doped.

How the invention may be put into effect will now be described with reference to the following examples.

WORKING EXAMPLES

Example 1

Be(BO)$_2$

Synthesis of bis(2-(2-hydroxyphenyl)benzoxazole)beryllium complex

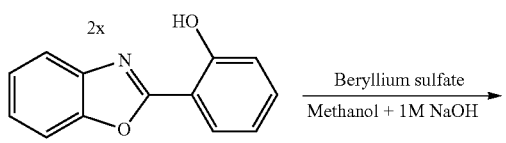
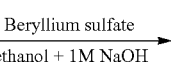

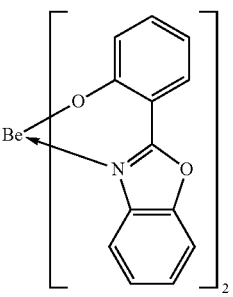

To a stirred suspension of beryllium sulfate (2.5 g, 14.11 mmol) in methanol (40 mL), was added a solution of 2-(2-hydroxyphenyl)benzoxazole (5.96 g, 28.23 mmol) in methanol (40 mL) at nitrogen atmosphere. The initial pale brown suspension slowly turned to a white suspension after slow addition of 1M sodium hydroxide (50 mL), and was left vigorously stirred overnight at room temperature under nitrogen atmosphere The white precipitate was filtered off, washed thoroughly with methanol (3×30 mL) and dried in vacuum oven for over 8 hours at 80° C. giving product 6.66 g (100% yield). It gave a purple/blue fluorescence. Sublimation (240° C., 10$^{-6}$ Torr.) yielded an analytical sample (13.3 g from 26.5 g); melting point at 268° C. (DSC peak).

Example 2

Be(BT)$_2$

Synthesis of bis(2-(2-hydroxyphenyl)benzothiazole)beryllium complex

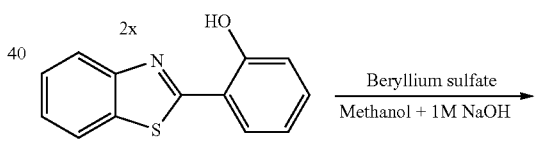

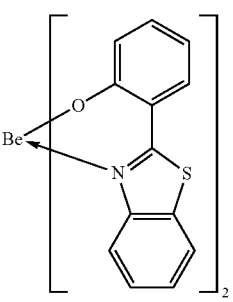

To a stirred suspension of beryllium sulfate (2.5 g, 14.11 mmol) in methanol (40 mL), was added a solution of 2-(2-hydroxyphenyl)benzothiazole (6.42 g, 28.23 mmol) in methanol (40 mL) at nitrogen atmosphere. The initial white suspension slowly turned to a yellowish suspension after slow addition of 1M sodium hydroxide (50 mL), and was left vigorously stirred overnight at room temperature under nitrogen atmosphere. The yellow precipitate was filtered off, washed thoroughly with methanol (3×30 mL) and dried in vacuum oven for over 8 hours at 80° C. giving product 7.30 g (100% yield). It gave a blue fluorescence. Sublimation (280° C., 10$^{-6}$ Torr.) yielded an analytical sample (9.3 g from 26.0 g); melting point at 330° C. (DSC peak).

Example 3

Be(5MeBO)$_2$

Synthesis of 2-(2-hydroxyphenyl)-5-methyl-benzoxazole

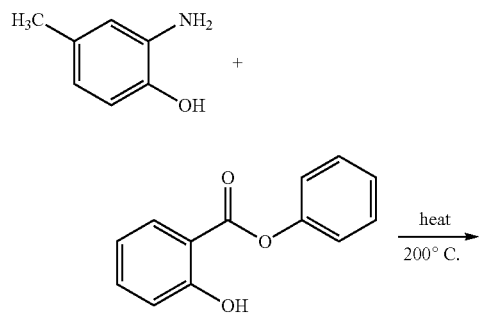

A mixture of 2-amino-p-cresol (10.0 g, 0.081 mole) and phenyl salicylate (17.4 g, 0.08 mole) was heated under nitrogen atmosphere in an oil bath at 200° C. for 1½ h. To the cooled reaction mixture ethanol was added and the product filtered off under suction. The product was dried under vacuum at 75° C., and then purified by column chromatography (dichloromethane). The eluent containing the product was concentrated and ethanol added to the residue to give a bright white crystalline solid. The product was suction filtered and dried under vacuum at 75° C. Yield 7.4 g (40%). M.p 138° C. (DSC, onset). Elemental analysis: Found, C 74.62, H 4.86 and N 6.32%. C$_{14}$H$_{11}$NO$_2$ requires C 74.65, H 4.92 and N 6.22%.

Synthesis of bis(2-(2-hydroxyphenyl)-5-methyl-benzoxazole)beryllium complex

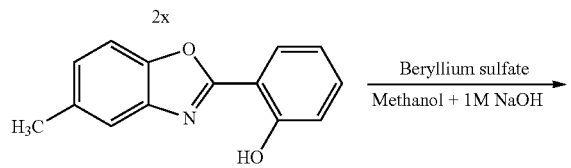

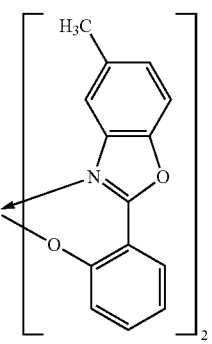

To a stirred suspension of beryllium sulfate (2.1 g, 11.86 mmol) in methanol (30 mL), was added a solution of 2-(2-hydroxyphenyl)-5-methyl-benzoxazole (5.5 g, 24.41 mmol) in methanol (30 mL) at nitrogen atmosphere. The initial pale brown suspension slowly turned to a creamy white suspension after slow addition of 1M sodium hydroxide (70 mL), and was left vigorously stirred overnight at room temperature under nitrogen atmosphere The white precipitate was filtered off, washed thoroughly with methanol (3×30 mL) and dried in vacuum oven for over 8 hours at 80° C., giving 6.40 g of product (100% yield). It gave a purple/blue fluorescence. Sublimation (235° C., 10$^{-6}$ Torr.) yielded an analytical sample (1.5 g from 6.4 g); melting point at 292° C. (DSC peak).

Example 4

Sc(BO)$_3$

Synthesis of tris(2-(2-hydroxyphenyl)benzoxazole)scandium complex

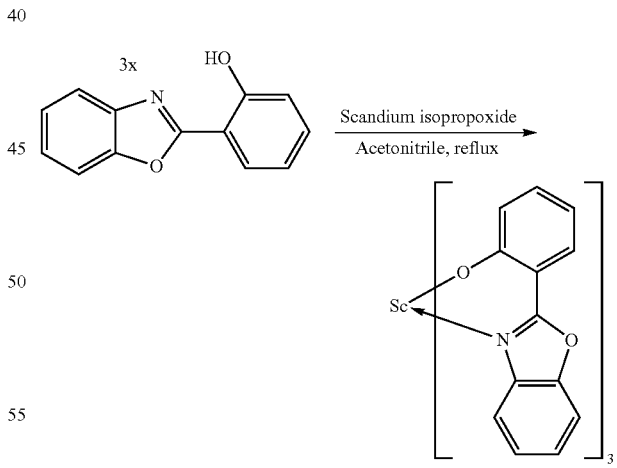

To a stirred solution of scandium isopropoxide (2.00 g, 9.00 mmol) in acetonitrile (40 mL), was added a suspension of 2-(2-hydroxyphenyl)benzoxazole (5.70 g, 27.00 mmol) in acetonitrile (40 mL) under nitrogen atmosphere. A creamy white suspension was observed after a few minutes of stirring, which was refluxed for 4 hours and stirred overnight at room temperature. The creamy white solid was filtered off, washed thoroughly with acetonitrile and dried in vacuum oven at 80° C. for 8 hours giving 3.7 g of product (62% yield). Sublimation (325° C., $10^{-6}$ Torr.) yielded an analytical sample (4.8 g from 5.8 g); melting point at 339° C. (DSC peak).

Example 5

Sc(BT)$_3$

Synthesis of tris(2-(2-hydroxyphenyl)benzothiazole)scandium complex

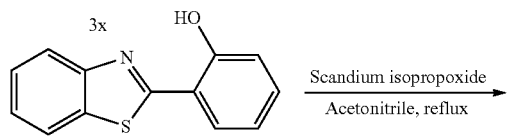

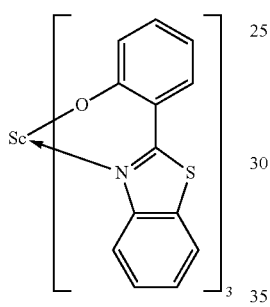

To a stirred solution of scandium isopropoxide (2.00 g, 9.00 mmol) in acetonitrile (40 mL), was added a suspension of 2-(2-hydroxyphenyl)benzothiazole (6.14 g, 27.01 mmol) in acetonitrile (40 mL) under nitrogen atmosphere. A yellow suspension was observed after a few minutes of stirring, which was refluxed for 6 hours and stirred overnight at room temperature. The yellow solid was filtered off, washed thoroughly with acetonitrile and dried in vacuum oven at 80° C. for 8 hours giving 6.5 g of product (100% yield). Sublimation (350° C., $10^{-6}$ Torr.) yielded an analytical sample (4.3 g from 6.3 g); melting point at 395° C. (DSC peak).

Example 6

Mg(BO)$_2$

Synthesis of bis(2-(2-hydroxyphenyl)benzoxazole)magnesium complex

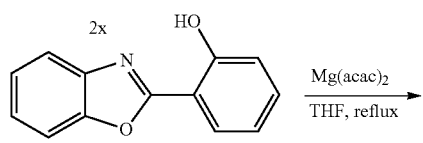

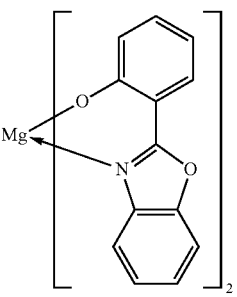

To a stirred solution of magnesium acetylacetonate (3.16 g, 14.20 mmol) in THF (40 mL), was added a suspension of 2-(2-hydroxyphenyl)benzoxazole (6.00 g, 28.40 mmol) in THF (40 mL) under nitrogen atmosphere. A creamy suspension was observed after a few minutes of stirring, which was refluxed for 6 hours and stirred overnight at room temperature. The solution was reduced in volume, approximately 10 mL, and the creamy white solid was filtered off, washed thoroughly with THF, and dried in vacuum oven at 80° C. for 8 hours giving 5.57 g of product (88% yield). Sublimation (370° C., $10^{-6}$ Torr.) yielded an analytical sample (1.9 g from 5.4 g); melting point was not observed from DSC.

Example 7

Zr(BO)$_4$

Synthesis of tetra(2-(2-hydroxyphenyl)benzoxazole)zirconium complex

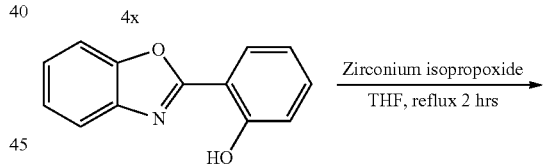

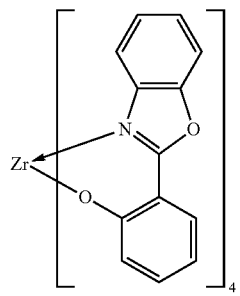

To a stirred solution of zirconium isopropoxide (2.7 g, 6.96 mmol) in THF (40 mL), was added a suspension of 2-(2-hydroxyphenyl)benzoxazole (6.0 g, 28.40 mmol) in THF (40 mL) under nitrogen atmosphere. A pale yellow suspension was observed after a few minutes of stirring, which was refluxed for 4 hours and stirred overnight at room temperature. The pale yellow solid was filtered off, washed thoroughly with THF and dried in vacuum oven at 80° C. for 8 hours giving 3.8 g of product (58% yield). Sublimation (290°

C., $10^{-6}$ Torr.) yielded an analytical sample (2.5 g from 3.6 g); melting point at 328° C. (DSC peak).

Example 8

Zr(BT)$_4$

Synthesis of tetra(2-(2-hydroxyphenyl)benzothiazole)zirconium complex

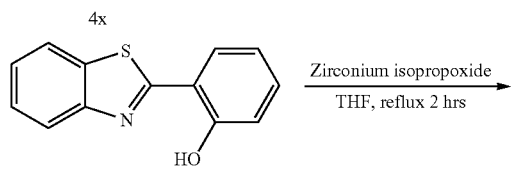

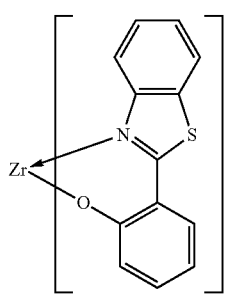

To a stirred solution of zirconium isopropoxide (5.0 g, 12.90 mmol) in THF (40 mL), was added a suspension of 2-(2-hydroxyphenyl)benzothiazole (11.7 g, 51.48 mmol) in THF (40 mL) under nitrogen atmosphere. A yellow suspension was observed after a few minutes of stirring, which was refluxed for 2 hours and stirred overnight at room temperature. The yellow solid was filtered off, washed thoroughly with THF and dried in vacuum oven at 80° C. for 8 hours giving 4.6 g of product (36% yield). Sublimation not successful (370° C., $10^{-6}$ Torr.); melting point of unsublimed product at 391° C. (DSC peak).

Example 9

Zr(5MeBO)$_4$

Synthesis of tetra(2-(2-hydroxyphenyl)-5-methyl-benzoxazole)zirconium complex

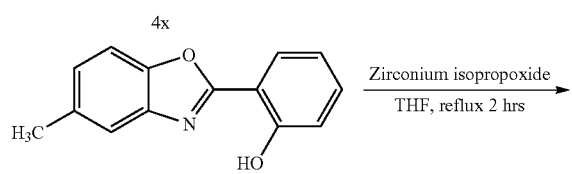

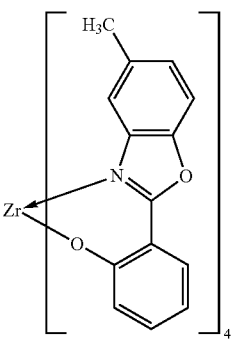

To a stirred suspension of zirconium isopropoxide (3.0 g, 7.76 mmol) in THF (30 mL), was added a solution of 2-(2-hydroxyphenyl)-5-methyl-benzoxazole (7.0 g, 31.07 mmol) in THF (30 mL) at nitrogen atmosphere. The initial pale brown suspension slowly turned to a creamy white suspension, refluxed for 2 hours and was left vigorously stirred overnight at room temperature under nitrogen atmosphere. The creamy white precipitate was filtered off, washed thoroughly with THF (3×30 mL) and dried in vacuum oven for over 8 hours at 80° C. giving 2.92 g of product (38% yield). It gave a purple/blue fluorescence. Sublimation (315° C., $10^{-6}$ Torr.) yielded an analytical sample (2.7 g from 2.9 g); melting point at 351° C. (DSC peak).

Example 10

Ba(BO)$_2$

Synthesis of bis(2-(2-hydroxyphenyl)benzoxazole)barium complex

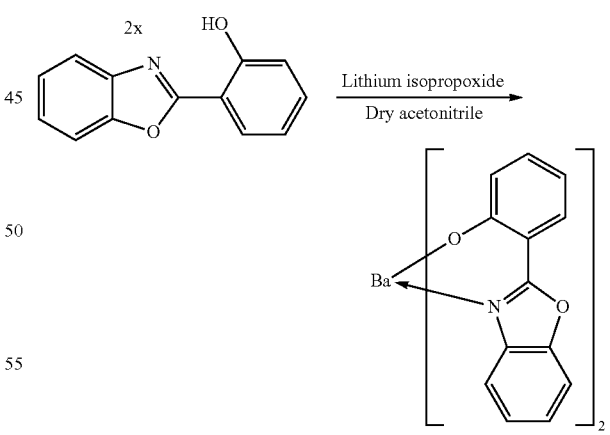

To a stirred suspension of barium acetylacetonate (2.5 g, 9.78 mmol) in dry acetonitrile (30 mL), was added a solution of 2-(2-hydroxyphenyl)benzoxazole (4.13 g, 19.57 mmol) in dry acetonitrile (20 mL) at nitrogen atmosphere. The pale brown suspension was refluxed for two hours and left vigorously stirred over the weekend. The creamy white precipitate was filtered off, washed thoroughly with acetonitrile (3×20 mL), dried in vacuum oven for over 8 hours at 80° C. giving 4.8 g of product (88% yield). Sublimation not successful, melting point at 227° C. (DSC peak).

Example 11

Ba(BT)$_2$

Synthesis of bis(2-(2-hydroxyphenyl)benzothiazole)barium complex

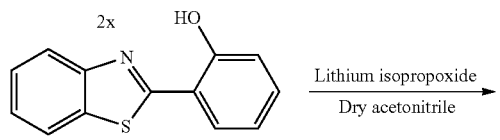

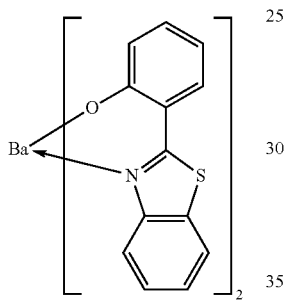

To a stirred suspension of barium acetylacetonate (2.5 g, 9.78 mmol) in dry acetonitrile (30 mL), was added a solution of 2-(2-hydroxyphenyl)benzothiazole (4.45 g, 19.58 mmol) in dry acetonitrile (20 mL) at nitrogen atmosphere. The pale yellow suspension was refluxed for two hours and left vigorously stirred over the weekend. The yellow precipitate was filtered off, washed thoroughly with acetonitrile (3×20 mL), dried in vacuum oven for over 8 hours at 80° C. giving 5.0 g of product (87% yield). Sublimation not successful (420° C., 10$^{-6}$ Torr.), melting point at 408° C. (DSC peak)

Example 12

Hf(BO)$_4$

Synthesis of tetrakis(2-(2-hydroxyphenyl)benzoxazole)hafnium complex

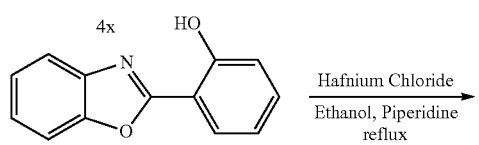

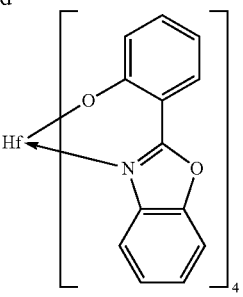

To a stirred solution of hafnium chloride (2.27 g, 7.10 mmol) in ethanol (40 mL), was added a solution of 2-(2-hydroxyphenyl)benzoxazole (6.00 g, 28.40 mmol) in ethanol (40 mL) under nitrogen atmosphere. The pH of the reaction mixture was increased with the addition of piperidine (~15 mL). A pale yellow suspension was observed after a few minutes of stirring, which was refluxed for 6 hours and stirred over the weekend at room temperature. The pale yellow precipitate was filtered off, washed thoroughly with ethanol (3×30 mL), dried in vacuum oven for 8 hours at 80° C. giving 6.04 g of product (95% yield). Sublimation not successful (260° C., 10$^{-6}$ Torr.), melting point at ~280° C. (broad DSC peak).

Example 13

Hf(BT)$_4$

Synthesis of tetrakis(2-(2-hydroxyphenyl)benzothiazole)hafnium complex

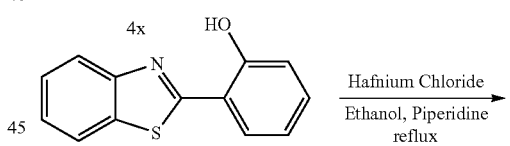

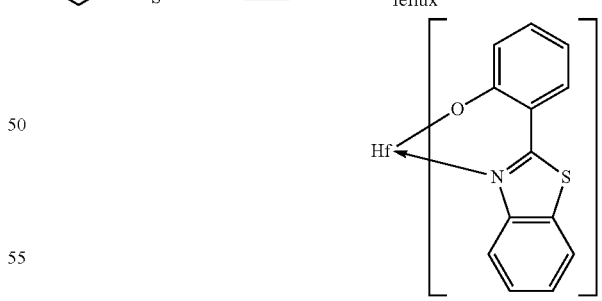

To a stirred solution of hafnium chloride (2.11 g, 6.60 mmol) in ethanol (40 mL), was added a solution of 2-(2-hydroxyphenyl)benzothiazole (6.00 g, 26.40 mmol) in ethanol (40 mL) under nitrogen atmosphere. The pH of the reaction mixture was increased with the addition of piperidine (~15 mL). A creamy yellow suspension was observed after a few minutes of stirring, which was refluxed for 6 hours and stirred over the weekend at room temperature. The pale yellow precipitate was filtered off, washed thoroughly with ethanol (3×30 mL), dried in vacuum oven for 8 hours at 80° C. giving 6.2 g of product (98% yield). Melting point at ~320° C. (broad DSC peak).

Example 14

Cu(BO)₂

Synthesis of the bis(2-(2-hydroxyphenyl)benzoxazole)copper complex

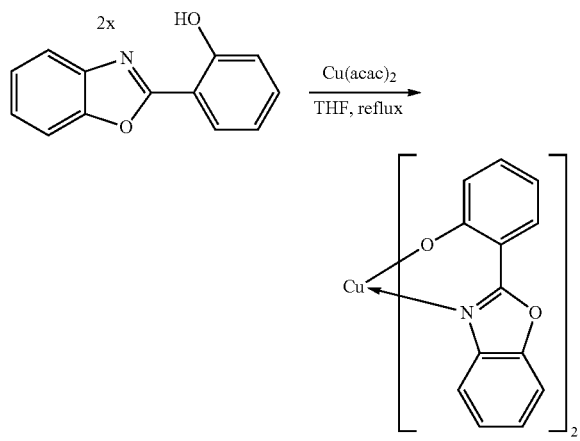

To a stirred solution of copper acetylacetonate (3.09 g, 11.83 mmol) in THF (30 mL), was added a suspension of 2-(2-hydroxyphenyl)benzoxazole (5.00 g, 23.67 mmol) in THF (30 mL) under nitrogen atmosphere. A brown suspension was observed after a few minutes of stirring, which was refluxed for 6 hours and stirred overnight at room temperature. The shiny brown solid was filtered off, washed thoroughly with THF, and dried in vacuum oven at 80° C. for 8 hours giving 5.6 g of product (98% yield). Melting point at 325° C. (DSC peak). Sublimation (295° C., 10⁻⁶ Torr.) yielded an analytical sample (4.2 g from 5.4 g); melting point at 329° C. (DSC peak).

Example 15

Y(BO)₃

Synthesis of tris(2-(2-hydroxyphenyl)benzoxazole)yttrium complex

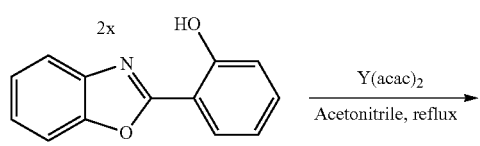

-continued

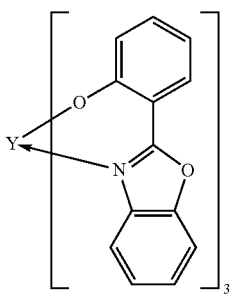

To a stirred solution of yttrium acetylacetonate (3.04 g, 7.89 mmol) in acetonitrile (30 mL), was added a suspension of 2-(2-hydroxyphenyl)benzoxazole (5.00 g, 23.67 mmol) in acetonitrile (30 mL) under nitrogen atmosphere. A creamy white suspension was observed after a few minutes of stirring, which was refluxed for 4 hours and stirred overnight at room temperature. The creamy white solid was filtered off, washed thoroughly with acetonitrile and dried in vacuum oven at 80° C. for 8 hours giving 4.4 g of product (78% yield). Sublimation (305° C., 10⁻⁶ Torr.) yielded an analytical sample (1.5 g from 4.4 g); melting point at ° C. (DSC peak).

Example 16

Y(BT)₃

Synthesis of tris(2-(2-hydroxyphenyl)benzothiazole)yttrium complex

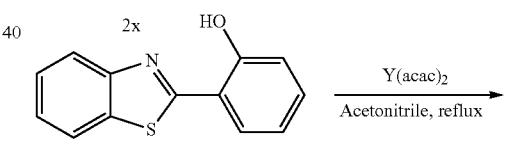

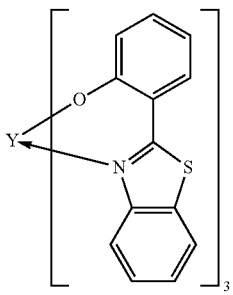

To a stirred solution of yttrium acetylacetonate (2.83 g, 7.33 mmol) in acetonitrile (30 mL), was added a suspension of 2-(2-hydroxyphenyl)benzothiazole (5.00 g, 22.00 mmol) in acetonitrile (30 mL) under nitrogen atmosphere. A pale yellow solution was observed after a few minutes of stirring, which was refluxed for 6 hours and stirred overnight at room temperature. The pale white solid was filtered off, washed thoroughly with acetonitrile and dried in vacuum oven at 80° C. for 8 hours giving 4.9 g of product (87% yield). Sublimation (350° C., 10⁻⁶ Torr.) yielded an analytical sample (1.4 g from 4.9 g); melting point was not observed from DSC.

Example 17

La(BO)₃

Synthesis of tris(2-(2-hydroxyphenyl)benzoxazole)lanthanum complex

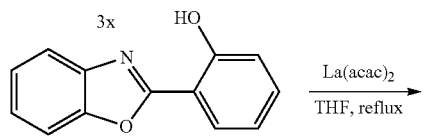

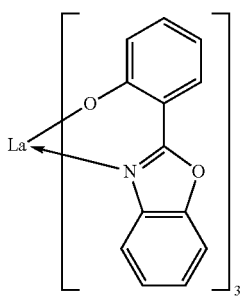

To a stirred solution of lanthanum acetylacetonate (3.44 g, 7.89 mmol) in THF (30 mL), was added a suspension of 2-(2-hydroxyphenyl)benzoxazole (5.00 g, 23.67 mmol) in THF (30 mL) under nitrogen atmosphere. A brown suspension was observed after a few minutes of stirring, which was refluxed for 6 hours and stirred over the weekend at room temperature. The pale white solid was filtered off, washed thoroughly with THF and dried in vacuum oven at 80° C. for 8 hours giving 0.65 g of product (11% yield).

Example 18

La(BT)₃

Synthesis of tris(2-(2-hydroxyphenyl)benzothiazole)lanthanum complex

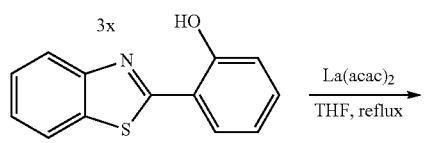

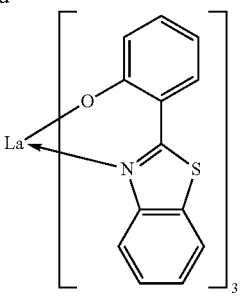

To a stirred solution of lanthanum acetylacetonate (3.19 g, 7.33 mmol) in THF (30 mL), was added a suspension of 2-(2-hydroxyphenyl)benzothiazole (5.00 g, 22.00 mmol) in THF (30 mL) under nitrogen atmosphere. A pale greenish suspension was observed after a few minutes of stirring, which was refluxed for 6 hours and stirred over the weekend at room temperature. The pale creamy white solid was filtered off, washed thoroughly with THF and dried in vacuum oven at 80° C. for 8 hours giving 1.37 g of product (23% yield).

Example 19

VO(BO)₂

Synthesis of bis(2-(2-hydroxyphenyl)benzoxazole)vanadium complex

To a stirred solution of vanadyl acetylacetonate (3.13 g, 11.80 mmol) in THF (30 mL), was added a suspension of 2-(2-hydroxyphenyl)benzoxazole (5.00 g, 23.67 mmol) in THF (30 mL) under nitrogen atmosphere. A brown suspension was observed after a few minutes of stirring, which was refluxed for 6 hours and stirred over the weekend at room temperature. The brown solid was filtered off, washed thoroughly with THF and dried in vacuum oven at 80° C. for 8 hours giving 4.7 g of product (82% yield). Sublimation (250°

C., 10$^{-6}$ Torr.) yielded an analytical sample (3.9 g from 4.7 g); melting point at N/A° C. (DSC peak).

Example 20

VO(BT)$_2$

Synthesis of bis-(2-(2-hydroxyphenyl)benzothiazole)vanadyl complex

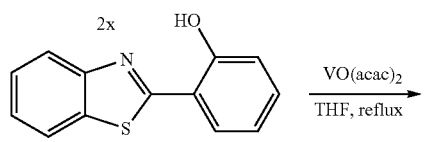

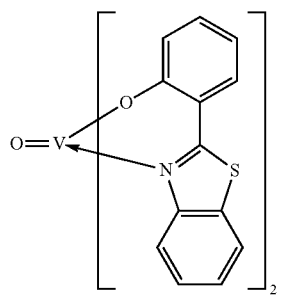

To a stirred solution of vanadyl acetylacetonate (2.91 g, 10.97 mmol) in THF (30 mL), was added a suspension of 2-(2-hydroxyphenyl)benzothiazole (5.00 g, 22.00 mmol) in THF (30 mL) under nitrogen atmosphere. A brown suspension was observed after a few minutes of stirring, which was refluxed for 6 hours and stirred over the weekend at room temperature. The brown solid was filtered off, washed thoroughly with THF and dried in vacuum oven at 80° C. for 8 hours giving 3.1 g of product (78% yield). Sublimation (250° C., 10$^{-6}$ Torr.) yielded an analytical sample (2.6 g from 3.1 g); melting point at 402° C. (DSC peak).

Example 21

Al(BO)$_3$

Synthesis of tris(2-(2-hydroxyphenyl)benzoxazole)aluminum complex

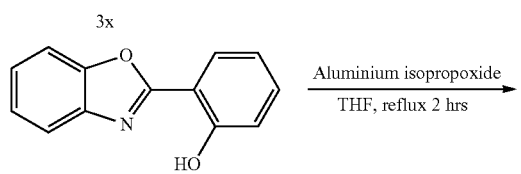

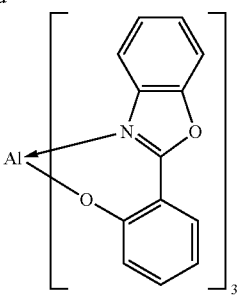

To a stirred solution of aluminium isopropoxide (5.0 g, 24.48 mmol) in THF (30 mL), was added a suspension of 2-(2-hydroxyphenyl)benzoxazole (15.51 g, 73.43 mmol) in THF (30 mL) under nitrogen atmosphere. A yellowish brown suspension was observed after a few minutes of stirring, which was refluxed for 2 hours and stirred overnight at room temperature. The creamy white solid was filtered off, washed thoroughly with THF, and dried in vacuum oven at 80° C. for 8 hours giving 10.18 g of product (63% yield). Sublimation (340° C., 10$^{-6}$ Torr.) yielded an analytical sample (2.6 g from 10.0 g); melting point at 298° C. (DSC peak).

Example 22

Yb(BO)$_3$

Synthesis of tris(2-(2-hydroxyphenyl)benzoxazole)ytterbium complex

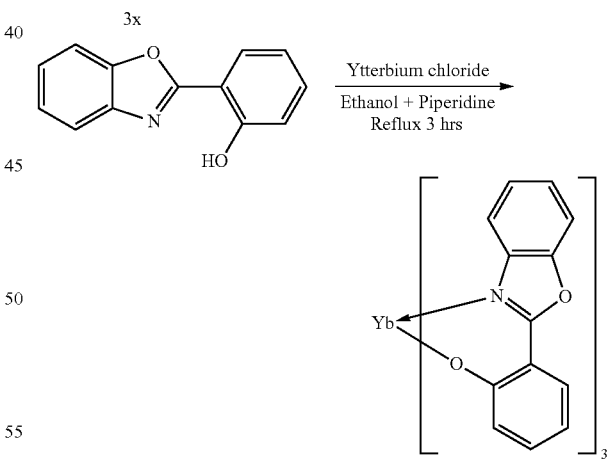

To a stirred solution of ytterbium chloride (2.00 g, 5.16 mmol) in ethanol (30 mL), was added a suspension of 2-(2-hydroxyphenyl)benzoxazole (3.27 g, 15.48 mmol) in ethanol (30 mL), followed by piperidine (5 mL) under nitrogen atmosphere. A creamy white suspension was observed after a few minutes of stirring, which was refluxed for 3 hours and stirred overnight at room temperature. The creamy white solid was filtered off, washed thoroughly with ethanol, and dried in vacuum oven at 80° C. for 8 hours. Giving 3.81 g of product (92% yield). Sublimation (350° C., 10⁻⁶ Torr.) yielded an analytical sample (3.2 g from 3.8 g); melting point at 413° C. (DSC peak).

Example 23

BO-Ph-DPB

Synthesis of 2-(2-Diphenylboroxy phenyl)benzoxazole

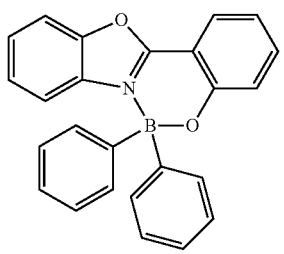

A solution of diphenylborinic anhydride (5.0 g; 0.014 mole) in tetrahydrofuran (20 ml) was added to a solution of 2-(2'-hydroxyphenyl)benzoxazole (3.1 g; 0.014 mole) in tetrahydrofuran (10 ml). The reaction mixture was refluxed under nitrogen for 2 h and allowed to cool to room temperature, then kept in the refrigerator for 18 h. The product was filtered off under suction, washed with methanol and dried under vacuum at 80° C. for 6 h. Yield 4.4 g (84%). The product was further purified by sublimation (85%). M.p 195° C. (DSC, onset); $T_g$ 59° C. Elemental analysis:

|  | ELEMENT |  |  |
|---|---|---|---|
|  | C | H | N |
| % Theory | 80.02 | 4.83 | 3.73 |
| % Found 1 | 79.83 | 4.80 | 3.85 |
| % Found 2 | 80.12 | 4.87 | 3.80 |

Example 24

BT-Ph-DPB

Synthesis of 2-(2-Diphenylboroxy phenyl)benzothiazole

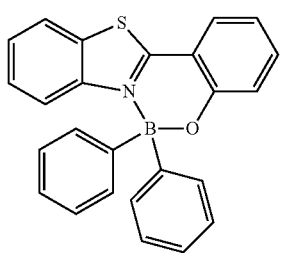

To a solution of 2-(2'-hydroxyphenyl)benzothiazole (3.25 g; 0.014 mole) in tetrahydrofuran (10 ml) was added to diphenylborinic anhydride (5.0 g; 0.014 mole), all at once. The solution became yellow in colour and a solid separated out immediately. Further, tetrahydrofuran (20 ml) was added and the reaction mixture was refluxed for 2 h under nitrogen atmosphere. The reaction mixture was allowed to cool and small amounts of methanol added to the reaction mixture. After cooling in the refrigerator overnight, the yellow fluorescent crystalline solid was filtered off under suction, washed with methanol and small amounts of diethyl ether. The product dried under vacuum at 80° C. Yield quantitative. The product was further purified by sublimation (92%). M.p 222° C. (DSC, onset); $T_g$ 76° C. Elemental analysis:

|  | ELEMENT |  |  |  |
|---|---|---|---|---|
|  | C | H | N | S |
| % Theory | 76.74 | 4.64 | 3.58 | 8.19 |
| % Found 1 | 76.82 | 4.60 | 3.64 | 8.30 |
| % Found 2 | 76.77 | 4.78 | 3.64 | 8.45 |

Example 25

5-MeBO-Np-DPB

Synthesis of 2-(5-Methylbenzoxazol-2-yl)-naphthalene-1-ol

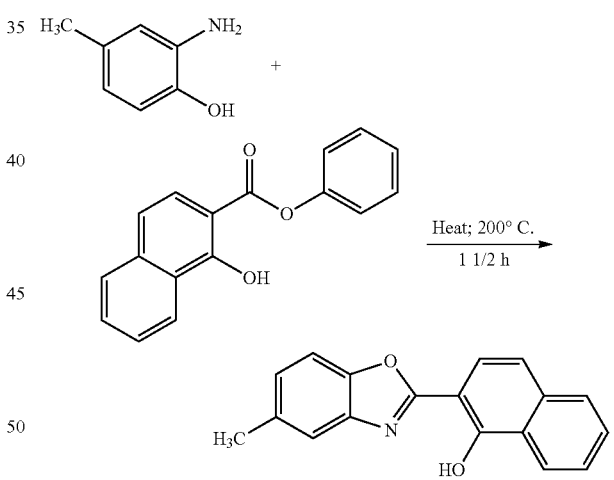

The compound was prepared by the above reaction without any solvent. Yield 84%; M.p 175° C. (DSC, onset). It was further purified by column chromatography (silica gel-CH₂Cl₂). Elemental analysis:

|  | ELEMENT |  |  |
|---|---|---|---|
|  | C | H | N |
| % Theory | 78.53 | 4.76 | 5.09 |
| % Found 1 | 78.72 | 4.69 | 5.12 |
| % Found 2 | 78.69 | 4.71 | 5.11 |

Synthesis of 2-(2-Diphenylboroxy napthyl)-5-methyl benzoxazole

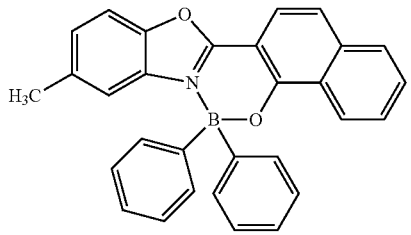

2-(2'-Hydroxy-1-naphthyl)-5-methyl benzoxazole (4.0; 0.0145 mole) was dissolved in tetrahydrofuran (30 ml) by warming the solution to 50° C. To the clear solution diphenylborinic anhydride (5.0 g; 0.014 mole) was added all at once. The solution became yellow in colour and a solid separated out immediately. The reaction mixture was refluxed for 2 h under nitrogen atmosphere and allowed to cool to room temperature. Small amounts of methanol added and the reaction mixture was kept in the refrigerator. The crystalline product was suction filtered, washed with methanol and dried under vacuum at 80° C. Yield 5.8 g (91%). The product was further purified by sublimation (95%). M.p 276° C. (DSC, onset); $T_g$ 89° C. Elemental analysis:

|  | ELEMENT | | |
| --- | --- | --- | --- |
|  | C | H | N |
| % Theory | 82.02 | 5.05 | 3.19 |
| % Found 1 | 82.04 | 5.08 | 3.28 |
| % Found 2 | 82.18 | 5.32 | 3.27 |

Example 26

BT-Np-DPB

Synthesis of 2-Benzothiazol-2-yl-naphthalene-1-ol

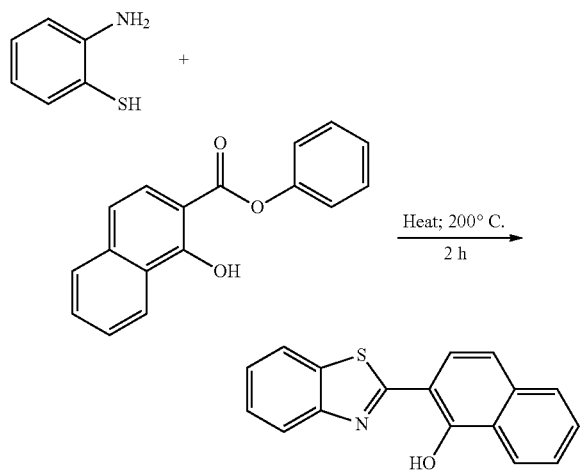

The compound was prepared by the above reaction without any solvent, isolated as a light greenish yellow solid after column chromatography over silica gel (dichloromethane-petroleum ether 40-60° C. 3:2). Yield 37%. M.p 181° C. (DSC, onset). Elemental analysis:

|  | ELEMENT | | | |
| --- | --- | --- | --- | --- |
|  | C | H | N | S |
| % Theory | 73.62 | 4.00 | 5.05 | 11.56 |
| % Found | 73.66 | 3.95 | 5.07 | 11.57 |

Synthesis of 2-(2-Diphenylboroxy napthyl)-benzothiazole

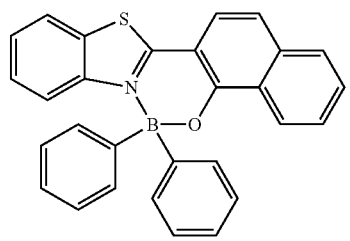

2-(1-Hydroxy-2-naphthyl)benzothiazole (4.0 g; 0.014 mole) was dissolved in tetrahydrofuran (30 ml) by warming the solution. To the magnetically stirred solution under nitrogen was added diphenyl borinic anhydride (5.0 g; 0.014 mole), all at once, followed by tetrahydrofuran (10 ml). A yellow solid separated out immediately. The reaction mixture was magnetically stirred and refluxed for 2 h and allowed to cool to room temperature. Little methanol (~5 ml) was added and the reaction mixture cooled in the refrigerator for 2 h. The product was filtered off under suction, washed with methanol and dried under vacuum at 80° C. for 8 h. Yield 5.9 g (93%). The product was further purified by sublimation (92%). M.p 269° C. (DSC, onset). Elemental analysis:

|  | ELEMENT | | | |
| --- | --- | --- | --- | --- |
|  | C | H | N | S |
| % Theory | 78.92 | 4.57 | 3.17 | 7.27 |
| % Found 1 | 78.79 | 4.62 | 3.20 | 7.23 |
| % Found 2 | 78.79 | 4.67 | 3.21 | 7.14 |

Example 27

Devices with green, blue and red emission were formed as follows. A pre-etched ITO coated glass piece (10×10 cm²) was used. The device was fabricated by sequentially forming layers on the ITO, by vacuum evaporation using a Solciet Machine, ULVAC Ltd. Chigacki, Japan. The active area of each pixel was 3 mm by 3 mm. The coated electrodes were encapsulated in an inert atmosphere (nitrogen) with UV-curable adhesive using a glass back plate. Electroluminescence studies were performed with the ITO electrode was always connected to the positive terminal. The current density vs. voltage studies were carried out on a computer controlled Keithly 2400 source meter.

Figure 2:
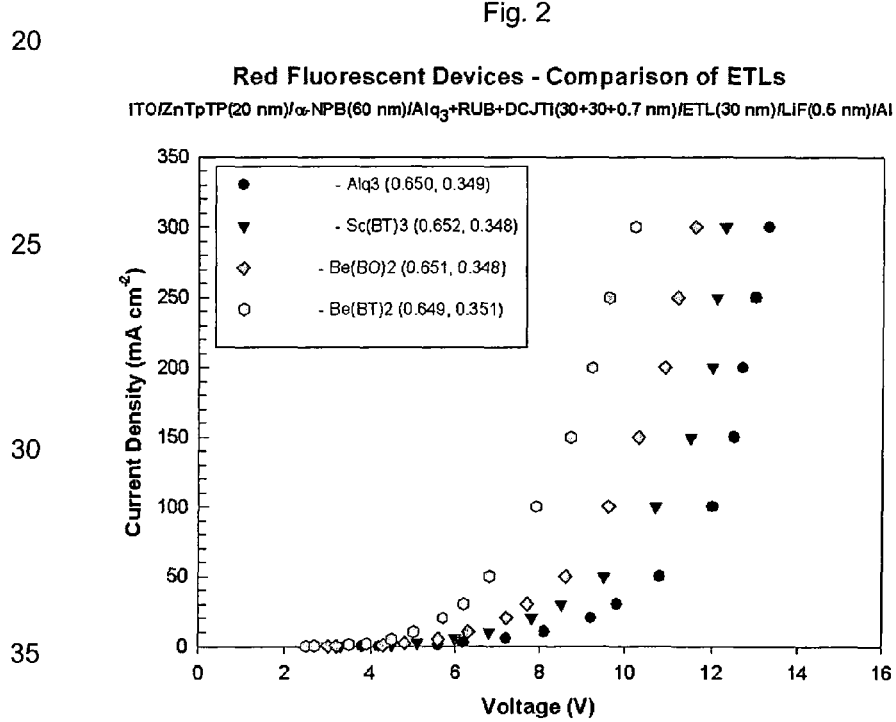
Figure 3:
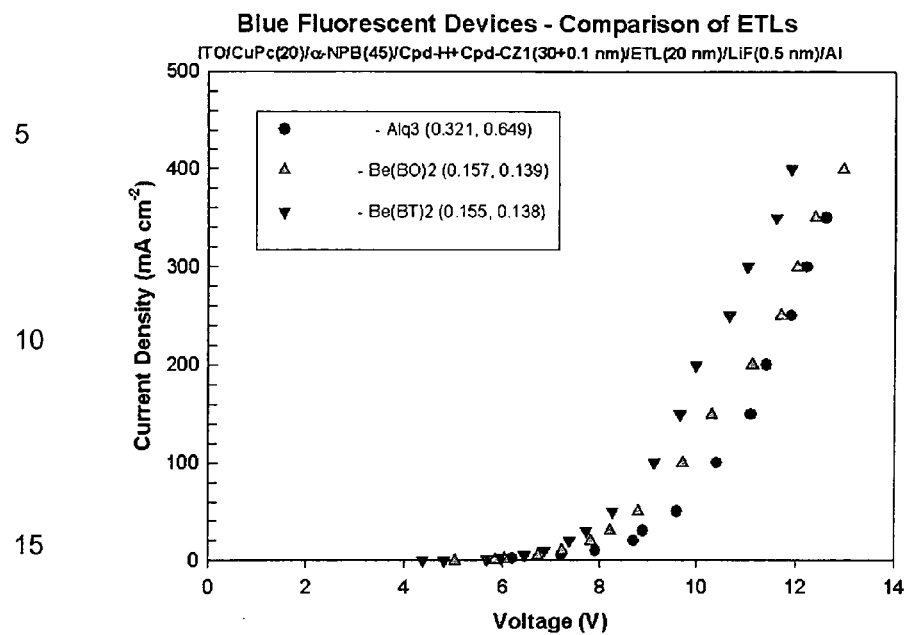
Figure 4:
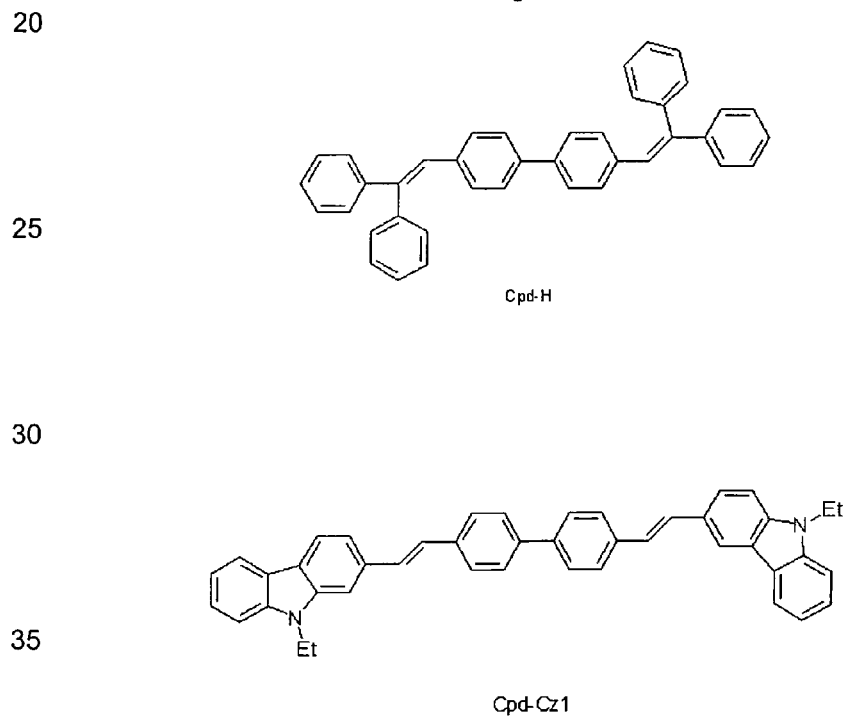

By the method described above devices consisting of an anode layer, buffer layer, hole transport layer, electroluminescent layer (doped material), electron transport layer, electron injection layer and cathode layer, the layer composition being as indicated in FIGS. 1 to 3 and film thicknesses being in nm. The CIE colour coordinates and other characteristics are as illustrated. Compounds used in these cells are shown in FIG. 4. It will be noted that embodiments of the compounds of formula I, II and III when incorporated as electron transport layers in OLEDs have exhibited a greater current density for a given voltage than corresponding devices where the electron transport material is aluminium quinolate.

The invention claimed is:

1. A compound of the formula III

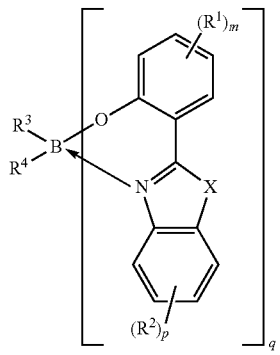

wherein

X represents oxygen or sulphur;

m and p are independently 0 to 4;

q is 1 to 4, depending on the valence of M;

$R^1$ and $R^2$ independently represent $C_1$ to $C_4$ alkyl or alkoxy, fluorine-substituted alkyl or alkoxy, fluoroalkyl, fluoroalkoxy, cycloalkyl or cycloalkoxy, aryl, heteroaryl, fluoro, cyano, aryl or heteroaryl substituted with one or more groups selected from $C_1$ to $C_4$ alkyl or alkoxy, fluorine-substituted alkyl or alkoxy, fluoroalkyl, fluoroalkoxy, fluoro or cyano, or when m or p is 2 to 4 represents fused cycloalkyl, aryl or heteroaryl which in turn is optionally substituted with one or more groups selected from $C_1$ to $C_4$ alkyl or alkoxy, fluorine-substituted alkyl or alkoxy, fluoroalkyl, fluoroalkoxy, fluoro or cyano; and $R^3$ and $R^4$ independently represent $C_1$ to $C_4$ alkyl, cyclopentyl, cyclohexyl or heteroaryl, the heteroaryl substituents optionally being substituted with one or more groups selected from $C_1$ to $C_4$ alkyl or alkoxy, fluorine-substituted alkyl or alkoxy, fluoroalkyl, fluoroalkoxy, fluoro or cyano.

2. The compound according to claim 1, wherein the ligand is selected from 2-(benzo[d]oxazol-2-yl)phenol, 2-(benzo[d]thiazol-2-yl)phenol, 2-(5-methylbenzo[d]oxazol-2-yl)phenol, 2-(benzo[d]oxazol-2-yl)naphthalen-1-ol, 2-(5-methylbenzo[d]oxazol-2-yl)naphthalen-1-ol, 2-(naphtho[1,2-d]oxazol-2-yl)phenol, 2-(benzo[d]thiazol-2-yl)phenol and 2-(benzo[d]thiazol-2-yl)naphthalen-1-ol.

3. The compound according to claim 2, wherein the compound is heteroleptic.

4. The compound according to claim 1, wherein the compound is heteroleptic.

5. An optical light emitting device having a first electrode, at least one layer comprising an electron transporting layer comprising the compound according to claim 1 and a second electrode.

6. An optical light emitting device having a first electrode, at least one electron transporting layer consisting of a compound of the formula I or III, or consisting of a mixture of a compound of the formula I or III and another electron transport material, or consisting of a mixture of a compound of the formula I or III and an n-doped donor type organic molecule,

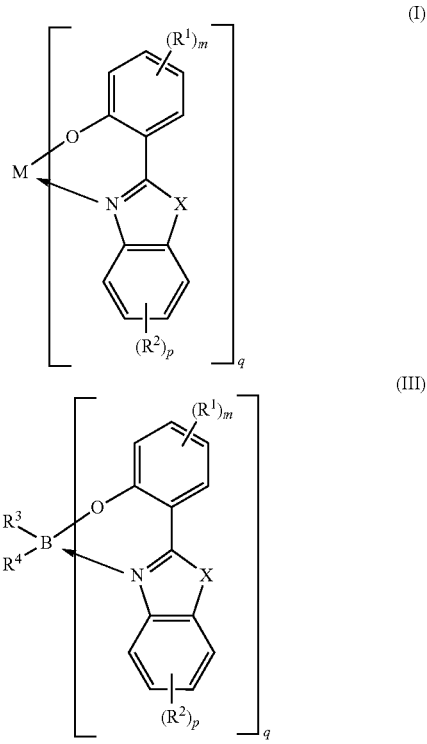

wherein

M represents Cu or a lanthanide;

X represents oxygen or sulphur;

m and p are independently 0 to 4;

q is 1 to 4, depending on the valence of M;

$R^1$ and $R^2$ independently represent $C_1$ to $C_4$ alkyl or alkoxy, fluorine-substituted alkyl or alkoxy, fluoroalkyl, fluoroalkoxy, cycloalkyl or cycloalkoxy, aryl, heteroaryl, fluoro, cyano, aryl or heteroaryl substituted with one or more groups selected from $C_1$ to $C_4$ alkyl or alkoxy, fluorine-substituted alkyl or alkoxy, fluoroalkyl, fluoroalkoxy, fluoro or cyano, or when m or p is 2 to 4 represents fused cycloalkyl, aryl or heteroaryl which in turn is optionally substituted with one or more groups selected from $C_1$ to $C_4$ alkyl or alkoxy, fluorine-substituted alkyl or alkoxy, fluoroalkyl, fluoroalkoxy, fluoro or cyano; and $R^3$ and $R^4$ independently represent $C_1$ to $C_4$ alkyl, cyclopentyl, cyclohexyl, aryl or heteroaryl, the aryl or heteroaryl substituents optionally being substituted with one or more groups selected from $C_1$ to $C_4$ alkyl or alkoxy, fluorine-substituted alkyl or alkoxy, fluoroalkyl, fluoroalkoxy, fluoro or cyano, and a second electrode.

7. The device according to claim 6, having one or more of the following features:
(a) a hole injection layer comprising a porphyrinic compound;
(b) a hole injection layer comprising ZnTpTP;
(c) a hole transport layer comprising an aromatic amine selected from NPD,

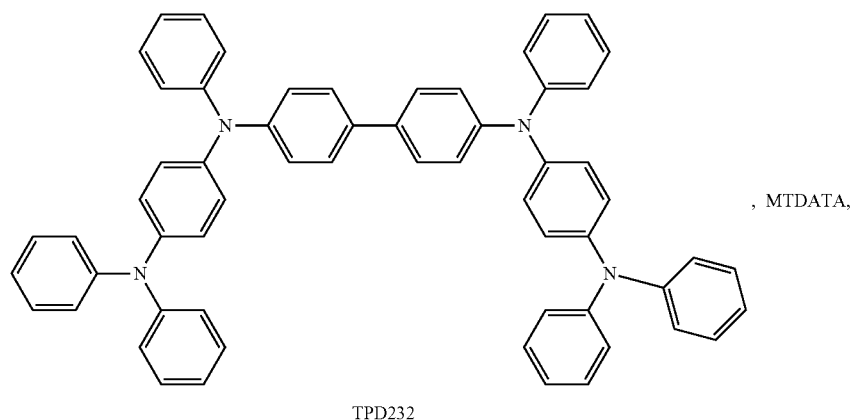
, MTDATA,
TPD232
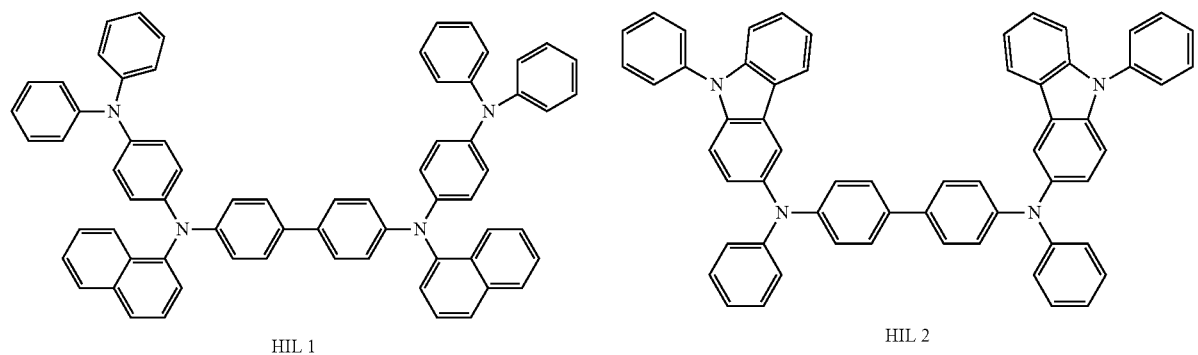
HIL 1                HIL 2
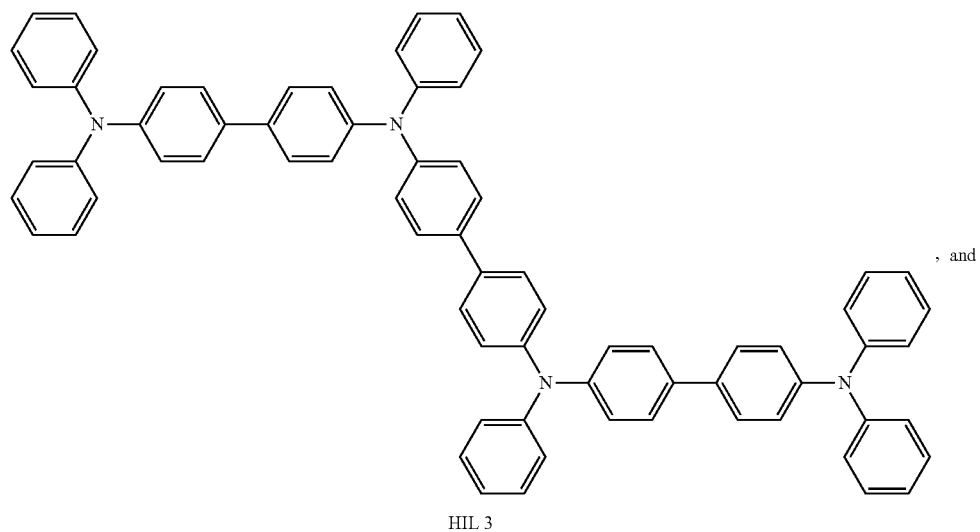
, and
HIL 3
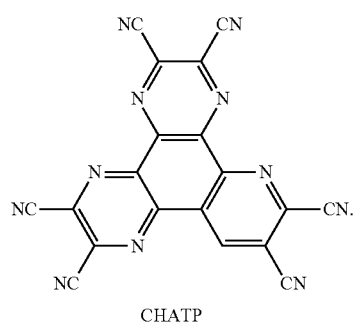
CHATP 8. The device according to claim 6, having one or more of the following features
   (a) a hole transport layer comprising at least one aromatic tertiary amine;
   (b) a hole transport layer comprising at least one of
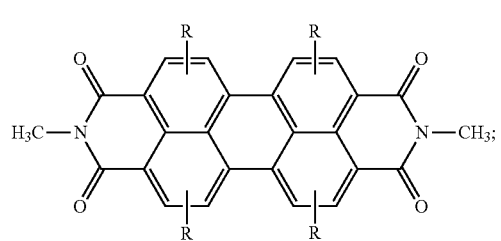
(i)
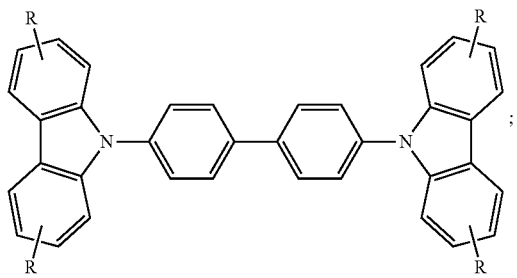
(ii)
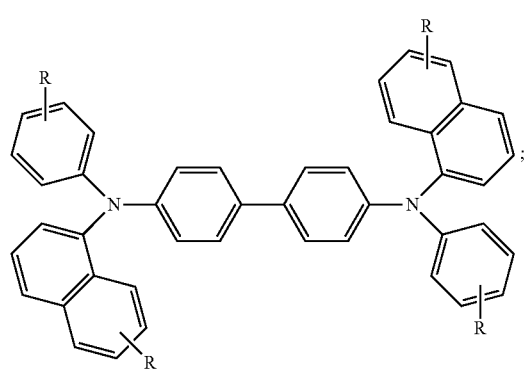
(iii)
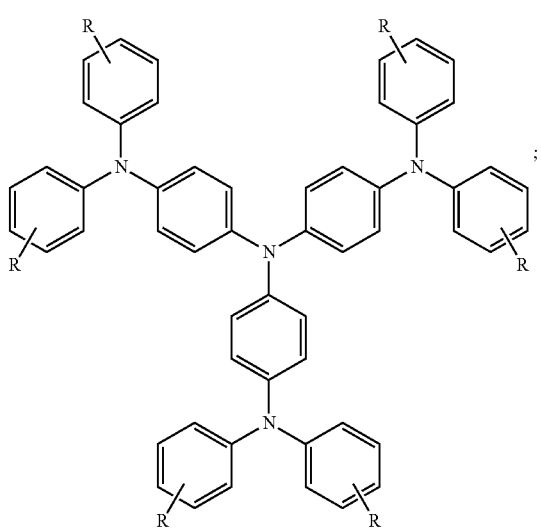
(iv)
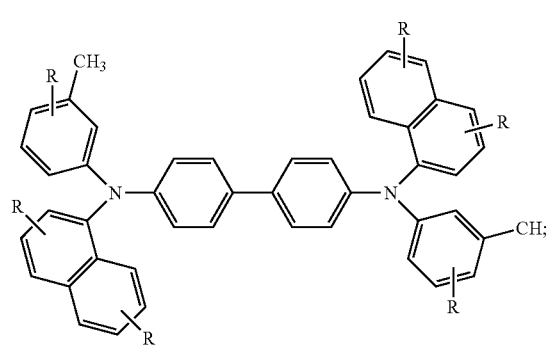
(v)
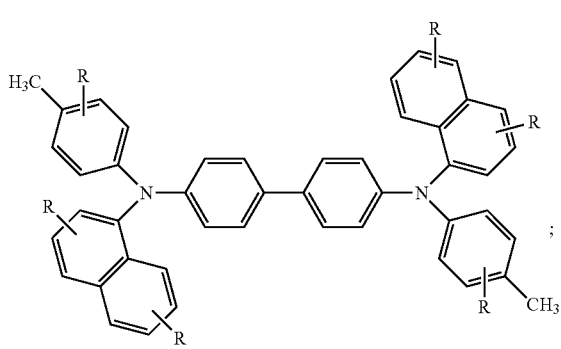
(vi)

-continued
(vii)
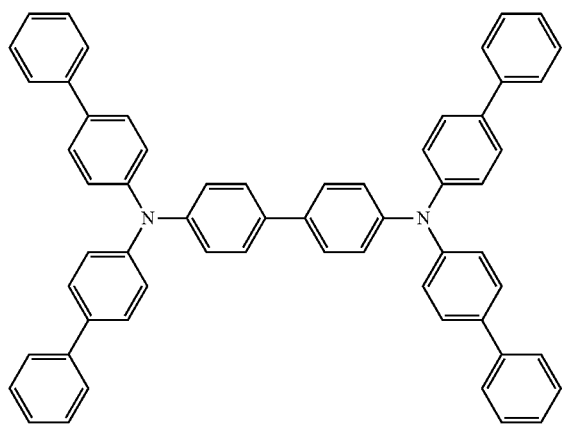
HTL1
(viii)
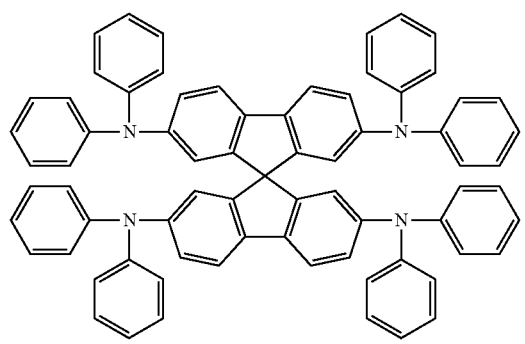
HTL2
(ix)
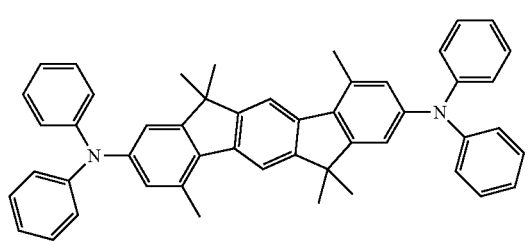
HTL3
(x)
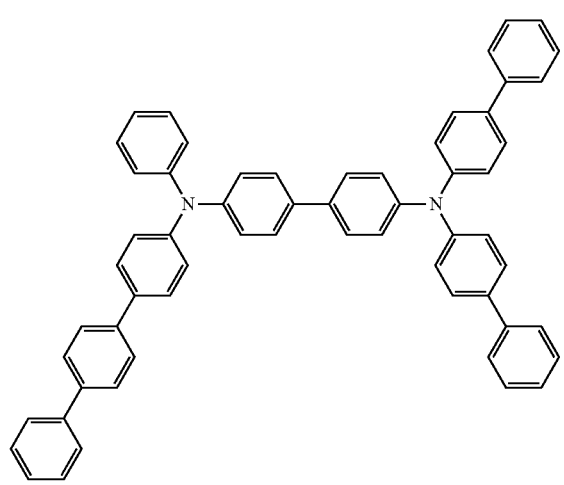
HTL4
(xi)
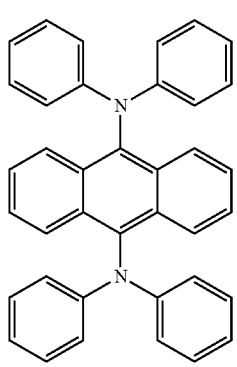
HTL5

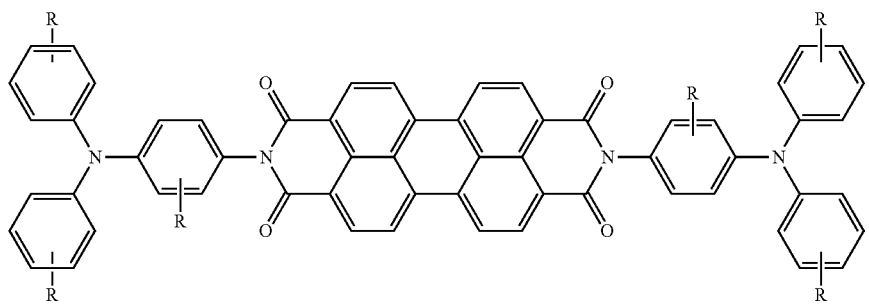
(xii)

wherein
the groups R in any of the formulae in (i) to (xii) can be the same or different and are selected from hydrogen; substituted and unsubstituted aliphatic groups; substituted and unsubstituted aromatic, heterocyclic and polycyclic ring structures; halogens; and thiophenyl groups;
and wherein in formula (i) the methyl groups is optionally replaced by $C_1$ to $C_4$ alkyl or monocyclic or polycyclic aryl or heteroaryl which is optionally further substituted with alkyl, aryl or arylamino;
(c) the hole transport layers comprising at least one compound of formula

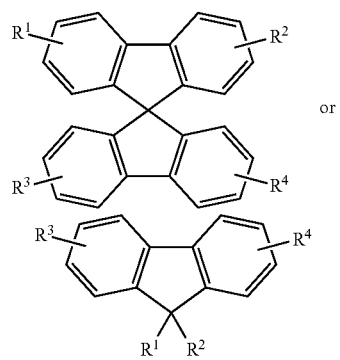

or wherein the groups $R^1$ to $R^4$ when appearing in either of the above formulae can be the same or different and are selected from hydrogen; substituted and unsubstituted aliphatic groups; substituted and unsubstituted aromatic, heterocyclic and polycyclic ring structures; halogens; and thiophenyl groups;
(d) the hole transport layer comprising α-NPB.

9. The device according to claim 6, having an electroluminescent layer, wherein the electroluminescent layer has one or more of the following features:
(a) it comprises at least one metal or metalloid complex;
(b) it comprises zirconium quinolate as host material doped with a dopant;
(c) it comprises aluminium quinolate as host material doped with a dopant;
(d) it comprises at least one iridium, ruthenium, osmium, rhodium, palladium or platinum complex, a boron complex or a rare earth complex;
(e) it comprises at least one aromatic tertiary amine as host material doped with at least one dopant;
(f) it comprises at least one light-emitting conjugated polymer or copolymer or a dendrimer;
(g) it comprises at least one host material selected from carbazols, ketones, phosphinoxides, sufoxides, bipolar hosts, and oligoarylenes selected from anthracenes, dinaphthyl anthracenes, benzanthracene anthracenes, tetraphenylspirobifluorenes;
(h) it comprises at least one dopant selected from phosphorescent emitters, diphenylacridine, coumarins, perylene, quinolates, porphoryin, porphines, pyrazalones and derivatives thereof or aryl amines; and
(i) there is up to 10 mole percent fluorescent material, based on moles of organo metallic complex.

10. The device according to claim 6, having an electroluminescent layer, wherein the electroluminescent layer has one or more of the following features:
(a) it comprises at least one metal or metalloid complex;
(b) it comprises zirconium quinolate as host material doped with a dopant;
(c) it comprises aluminium quinolate as host material doped with a dopant;
(d) it comprises at least one iridium, ruthenium, osmium, rhodium, palladium or platinum complex, a boron complex or a rare earth complex;
(e) it comprises at least one aromatic tertiary amine as host material doped with at least one dopant;
(f) it comprises at least one light-emitting conjugated polymer or copolymer or a dendrimer;
(g) it comprises at least one host material selected from carbazols, ketones, phosphinoxides, sufoxides, bipolar hosts, and oligoarylenes selected from anthracenes, dinaphthyl anthracenes, benzanthracene anthracenes, tetraphenylspirobifluorenes;
(h) it comprises at least one dopant selected from phosphorescent emitters, diphenylacridine, coumarins, perylene, quinolates, porphoryin, porphins, pyrazalones and derivatives thereof, indenofluorene monoamines and -diamines, benzofluorene monoamines and -diamines and dibenzoindenofluorene monoamines and -diamines;
(i) there is up to $10^{-3}$ mole percent fluorescent material, based on moles of organo metallic complex.

11. The device according to claim 6, having an electron injection layer based on an inorganic lithium compound or a lithium complex.

12. An imaging member for creation of an electrostatic latent image comprising at least one compound as claimed in claim 1.

13. A lamp comprising electroluminescent material and at least one compound according to claim 1 as an electron transport material.

14. The device according to claim 6, which is a flat panel display.

15. The device according to claim 14, which is a passive matrix display.

16. The device according to claim 14 which is an active matrix display.

* * * * *